United States Patent
Inouye et al.

(10) Patent No.: US 11,596,533 B2
(45) Date of Patent: Mar. 7, 2023

(54) PROJECTING MEMBER WITH BARB FOR CARDIOVASCULAR DEVICES

(71) Applicant: BOSTON SCIENTIFIC SCIMED, INC., Maple Grove, MN (US)

(72) Inventors: Joshua Mark Inouye, Maple Grove, MN (US); Brian Joseph Tischler, Shoreview, MN (US); Dennis A. Peiffer, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 547 days.

(21) Appl. No.: 16/546,561

(22) Filed: Aug. 21, 2019

(65) Prior Publication Data

US 2020/0060849 A1 Feb. 27, 2020

Related U.S. Application Data

(60) Provisional application No. 62/720,223, filed on Aug. 21, 2018.

(51) Int. Cl.
*A61F 2/848* (2013.01)
*A61B 17/12* (2006.01)
(Continued)

(52) U.S. Cl.
CPC ........ *A61F 2/848* (2013.01); *A61B 17/12109* (2013.01); *A61B 17/12159* (2013.01);
(Continued)

(58) Field of Classification Search
CPC .... A61F 2/848; A61F 2/90; A61F 2002/8483; A61F 2250/001; A61B 17/12109;
(Continued)

(56) References Cited

U.S. PATENT DOCUMENTS

| 178,283 A | 6/1876 | French |
| 1,967,318 A | 7/1934 | Monahan |

(Continued)

FOREIGN PATENT DOCUMENTS

| EP | 3072461 A1 | 9/2016 |
| WO | 9313712 A1 | 7/1993 |

(Continued)

OTHER PUBLICATIONS

International Search Report and Written Opinion dated Aug. 3, 2004 for International Application No. PCT/US2004/008109.

(Continued)

*Primary Examiner* — Thomas McEvoy
(74) *Attorney, Agent, or Firm* — Seager, Tufte & Wickhem

(57) ABSTRACT

A medical implant including an expandable framework configured to shift between a collapsed configuration and an expanded configuration, the expandable framework comprising a plurality of interconnected struts defining a plurality of cells; and an occlusive element connected to the expandable framework and having an inner surface and an outer surface. The expandable framework may include a plurality of securement members projecting from the plurality of interconnected struts. One of the inner surface or the outer surface of the occlusive element may be in contact with the plurality of interconnected struts, and the other of the inner surface and the outer surface not in contact with the plurality of interconnected struts may lie against an opposing surface of each of the plurality of securement members. A tip portion of the plurality of securement members may not extend radially outward of the plurality of interconnected struts.

19 Claims, 19 Drawing Sheets

(51) Int. Cl.
*A61F 2/90* (2013.01)
*A61B 17/00* (2006.01)

(52) U.S. Cl.
CPC ......... *A61B 17/12172* (2013.01); *A61F 2/90* (2013.01); *A61B 17/12118* (2013.01); *A61B 2017/00623* (2013.01); *A61B 2017/1205* (2013.01); *A61F 2002/8483* (2013.01); *A61F 2250/001* (2013.01)

(58) Field of Classification Search
CPC ........ A61B 17/12159; A61B 17/12172; A61B 17/12122
See application file for complete search history.

(56) References Cited

U.S. PATENT DOCUMENTS

| | | |
|---|---|---|
| 3,402,710 A | 9/1968 | Maurice |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,175,545 A | 11/1979 | Termanini |
| 4,309,776 A | 1/1982 | Berguer |
| 4,341,218 A | 7/1982 | Ü |
| 4,425,908 A | 1/1984 | Simon |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,683,411 A | 11/1997 | Kavteladze et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,733,325 A * | 3/1998 | Robinson .............. A61F 2/9525 623/1.11 |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Lentz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,820,591 A | 10/1998 | Thompson et al. |
| 5,823,198 A | 10/1998 | Jones et al. |
| 5,830,228 A | 11/1998 | Knapp et al. |

(56) References Cited

U.S. PATENT DOCUMENTS

| | | |
|---|---|---|
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muij Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,776 B1 | 7/2001 | O'Connell |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,361,545 B1 | 3/2002 | Macoviak et al. |
| 6,364,895 B1 | 4/2002 | Greenhalgh |
| 6,368,338 B1 | 4/2002 | Konya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,468,301 B1 | 10/2002 | Amplatz et al. |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,589,251 B2 | 7/2003 | Yee et al. |
| 6,599,308 B2 | 7/2003 | Amplatz |
| 6,623,508 B2 | 9/2003 | Shaw et al. |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,726,701 B2 | 4/2004 | Gilson et al. |

(56) References Cited

U.S. PATENT DOCUMENTS

| | | | |
|---|---|---|---|
| 6,730,108 B2 | 5/2004 | Van Tassel et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,949,113 B2 | 9/2005 | Van Tassel et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,044,134 B2 | 5/2006 | Khairkhahan et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,713,282 B2 | 5/2010 | Frazier et al. |
| 7,722,641 B2 | 5/2010 | van der Burg et al. |
| 7,799,049 B2 | 9/2010 | Ostrovsky et al. |
| 7,811,300 B2 | 10/2010 | Feller, III et al. |
| 8,025,495 B2 | 9/2011 | Hardert et al. |
| 8,043,329 B2 | 10/2011 | Khairkhahan et al. |
| 8,080,032 B2 | 12/2011 | van der Burg et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,663,273 B2 | 3/2014 | Khairkhahan et al. |
| 8,685,055 B2 | 4/2014 | VanTassel et al. |
| 8,834,519 B2 | 9/2014 | van der Burg et al. |
| 9,211,124 B2 | 12/2015 | Campbell et al. |
| 9,554,806 B2 | 1/2017 | Larsen et al. |
| 9,943,299 B2 | 4/2018 | Khairkhahan et al. |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0220667 A1 | 11/2003 | van der Burg et al. |
| 2004/0034366 A1 | 2/2004 | van der Burg et al. |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0220610 A1 | 11/2004 | Kreidler et al. |
| 2004/0230222 A1 | 11/2004 | van der Burg et al. |
| 2005/0203568 A1 | 9/2005 | Burg et al. |
| 2009/0149945 A1* | 6/2009 | Pike ........................ A61F 2/915 623/1.36 |
| 2009/0270972 A1* | 10/2009 | Lane ..................... A61F 2/2418 623/1.14 |
| 2012/0172927 A1 | 7/2012 | Campbell et al. |
| 2012/0191174 A1* | 7/2012 | Vinluan ................. A61F 2/958 623/1.12 |
| 2013/0165735 A1 | 6/2013 | Khairkhahan et al. |
| 2014/0018841 A1 | 1/2014 | Peiffer et al. |
| 2014/0100596 A1 | 4/2014 | Rudman et al. |
| 2014/0148842 A1 | 5/2014 | Khairkhahan et al. |
| 2014/0303719 A1 | 10/2014 | Cox et al. |
| 2015/0080903 A1 | 3/2015 | Dillard et al. |
| 2015/0196300 A1 | 7/2015 | Tischler et al. |
| 2016/0192942 A1 | 7/2016 | Strauss et al. |
| 2016/0331382 A1 | 11/2016 | Center et al. |
| 2017/0056166 A1 | 3/2017 | Ratz et al. |
| 2017/0181751 A1 | 6/2017 | Larsen et al. |

FOREIGN PATENT DOCUMENTS

| | | |
|---|---|---|
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0108743 A1 | 2/2001 |
| WO | 0115629 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A1 | 3/2002 |
| WO | 02071977 A1 | 9/2002 |
| WO | 03007825 A1 | 1/2003 |
| WO | 03008030 A1 | 1/2003 |
| WO | 03032818 A1 | 4/2003 |
| WO | 2010081033 A1 | 7/2010 |
| WO | 2013159065 A1 | 10/2013 |
| WO | 2019084358 A1 | 5/2019 |

OTHER PUBLICATIONS

International Search Report and Written Opinion dated Feb. 15, 2000 for International Application No. PCT/US99/26325.

International Search Report and Written Opinion dated May 20, 2003 for International Application No. PCT/US02/33808.

Written Opinion dated Nov. 17, 2003 for International Application No. PCT/US/02/33808.

International Search Report and Written Opinion dated Aug. 21, 2018 for International Application No. PCT/US2018/029684.

International Search Report and Written Opinion dated Oct. 14, 2019 for International Application No. PCT/US2019/047452.

* cited by examiner

PROJECTING MEMBER WITH BARB FOR CARDIOVASCULAR DEVICES

CROSS-REFERENCE TO RELATED APPLICATIONS

This application claims the benefit of priority under 35 U.S.C. § 119 to U.S. Provisional Application Ser. No. 62/720,223, filed Aug. 21, 2018, the entirety of which is incorporated herein by reference.

TECHNICAL FIELD

The disclosure relates generally to percutaneous medical implants and more particularly to cardiovascular medical implants for delivery into the left atrial appendage (LAA) and/or the valve(s) of a heart.

BACKGROUND

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Atrial fibrillation (AF) a common sustained cardiac arrhythmia affecting over 5.5 million people worldwide. Atrial fibrillation is the irregular, chaotic beating of the upper chambers of the heart. Electrical impulses discharge so rapidly that the atrial muscle quivers, or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein is a medical device system that may be used for delivering a medical device to a portion of the cardiovascular system in order to diagnose, treat, and/or repair the system. At least some of the medical devices disclosed herein may be used to deliver and implant a replacement heart valve implant (e.g., a replacement aortic valve, replacement mitral valve, etc.). In addition, the medical device system disclosed herein may deliver the replacement heart valve implant percutaneously and, thus, may be much less invasive to the patient.

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a medical implant may comprise an expandable framework configured to shift between a collapsed configuration and an expanded configuration, the expandable framework comprising a plurality of interconnected struts defining a plurality of cells; and an occlusive element connected to the expandable framework and having an inner surface and an outer surface. The expandable framework may include a plurality of securement members projecting from the plurality of interconnected struts. One of the inner surface or the outer surface of the occlusive element may be in contact with the plurality of interconnected struts, and the other of the inner surface and the outer surface not in contact with the plurality of interconnected struts may lie against an opposing surface of each of the plurality of securement members.

In addition or alternatively, and in a second aspect, each of the plurality of securement members includes a base portion attached to the plurality of interconnected struts, a tip portion, and a body portion extending from the base portion to the tip portion.

In addition or alternatively, and in a third aspect, the tip portion is circumferentially aligned with the plurality of interconnected struts.

In addition or alternatively, and in a fourth aspect, the tip portion extends axially toward an inflow end of the occlusive element.

In addition or alternatively, and in a fifth aspect, the body portion extends axially toward an inflow end of the occlusive element.

In addition or alternatively, and in a sixth aspect, at least some of the plurality of securement members each have a barb projecting circumferentially therefrom.

In addition or alternatively, and in a seventh aspect, the barb projecting circumferentially from at least some of the plurality of securement members projects from the body portion of its respective securement member.

In addition or alternatively, and in an eighth aspect, each barb includes a forward surface facing towards the tip portion of its respective securement member, and a rear surface facing towards the base of its respective securement member.

In addition or alternatively, and in a ninth aspect, the rear surface is positioned at an obtuse angle to the body portion.

In addition or alternatively, and in a tenth aspect, the rear surface is positioned at an acute angle to the body portion.

In addition or alternatively, and in an eleventh aspect, the forward surface is positioned at an obtuse angle to the body portion.

In addition or alternatively, and in a twelfth aspect, the expandable framework and the plurality of securement members are formed from a unitary tubular member.

In addition or alternatively, and in a thirteenth aspect, a medical implant may comprise an expandable framework configured to shift between a collapsed configuration and an expanded configuration, the expandable framework comprising a plurality of interconnected struts defining a plurality of cells; and an occlusive element connected to the expandable framework and having an inner surface and an outer surface. The expandable framework includes a plurality of securement members projecting from the plurality of interconnected struts. One of the inner surface or the outer surface of the occlusive element may be in contact with the plurality of interconnected struts, and the other of the inner surface or the outer surface not in contact with the plurality of interconnected struts may lie against an opposing surface of each of the plurality of securement members. A tip portion of each of the plurality of securement members does not extend radially outward of the plurality of interconnected struts.

In addition or alternatively, and in a fourteenth aspect, each of the plurality of securement members includes a body portion having an offset extending radially outward of the plurality of interconnected struts.

In addition or alternatively, and in a fifteenth aspect, the occlusive element is disposed radially inward of the offset.

In addition or alternatively, and in a sixteenth aspect, the inner surface of the occlusive element is in contact with the plurality of interconnected struts, and the outer surface of the occlusive element faces an inner surface of the offset.

In addition or alternatively, and in a seventeenth aspect, a replacement heart valve implant may comprise an expandable framework configured to shift between a collapsed configuration and an expanded configuration, the expandable framework comprising a plurality of interconnected struts defining a plurality of cells; and at least one valve leaflet connected to the expandable framework and disposed within the expandable framework, the at least one valve leaflet each having an inner surface and an outer surface. The expandable framework includes a plurality of securement members projecting from the plurality of interconnected struts, each of the plurality of securement members including a base portion attached to the plurality of interconnected struts, a tip portion, and a body portion extending axially from the base portion to the tip portion, the body portion having an offset extending radially inward of the plurality of interconnected struts. The outer surface of the at least one valve leaflet may be in contact with the plurality of interconnected struts, and the inner surface of the at least one valve leaflet may face an outer surface of the body portion of each of the plurality of securement members.

In addition or alternatively, and in an eighteenth aspect, the tip portion of each of the plurality of securement members is disposed radially outward of the at least one valve leaflet.

In addition or alternatively, and in a nineteenth aspect, the tip portion of each of the plurality of securement members does not extend radially outward of the plurality of interconnected struts.

In addition or alternatively, and in a twentieth aspect, the tip portion of each of the plurality of securement members is offset from and substantially parallel to the body portion.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
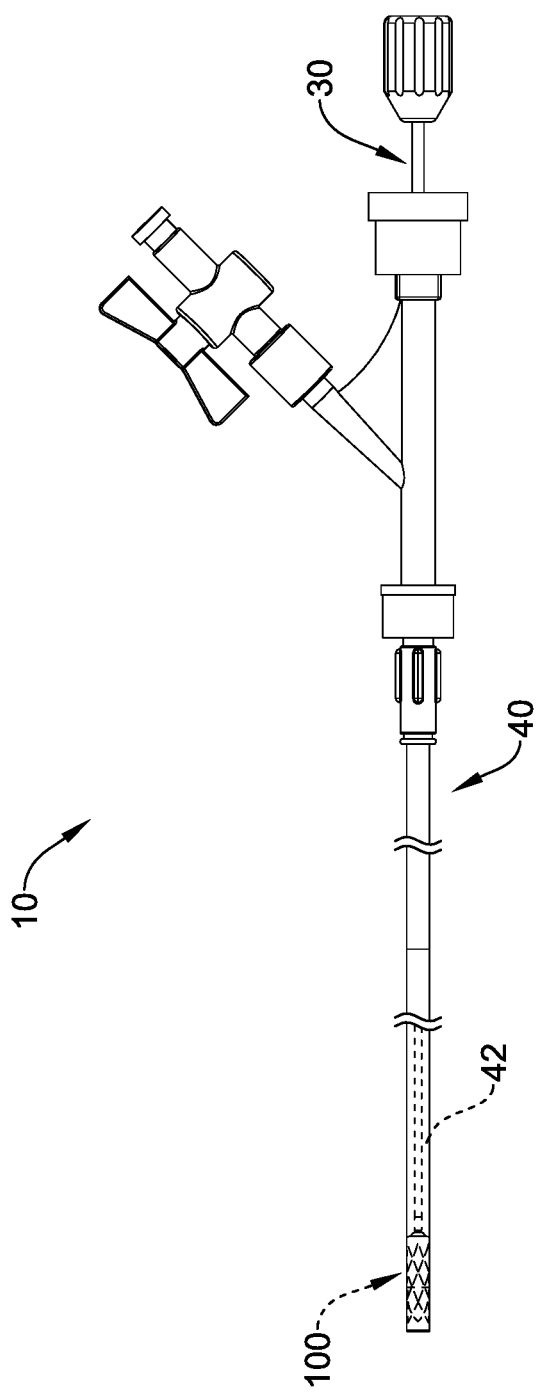
FIGS. 1-2 are side views of an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 2:
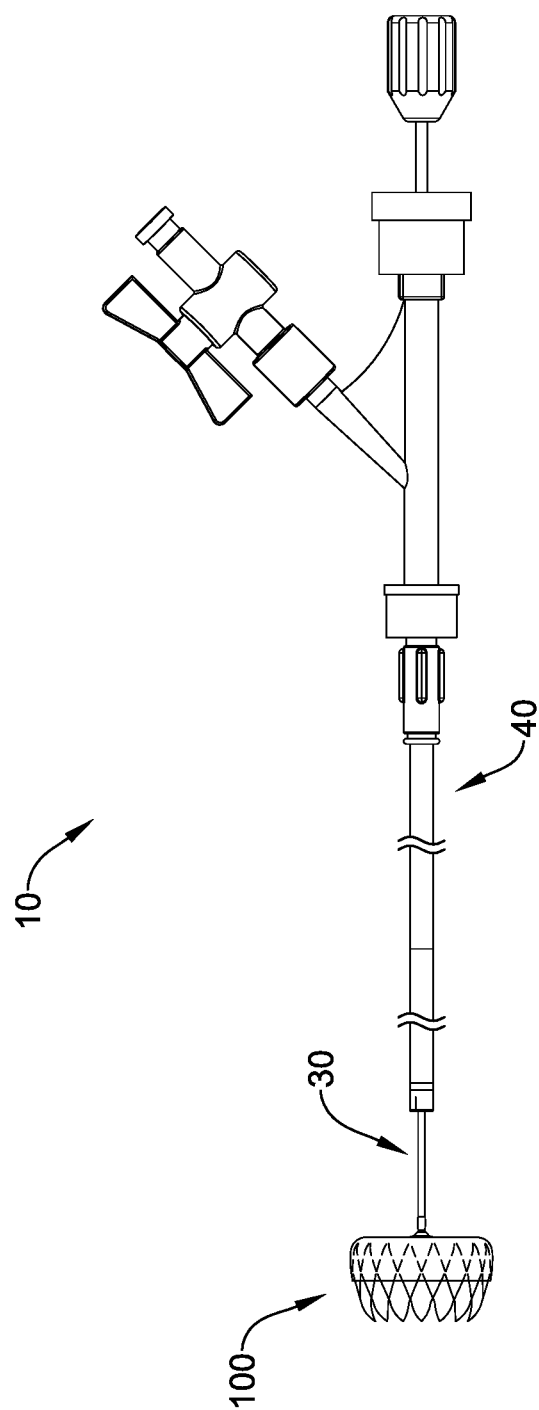

The figures illustrate selected components and/or arrangements of a medical device system 10, shown schematically in FIGS. 1-2 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical implants (e.g., a cardiovascular medical implant, an occlusive medical implant, a replacement heart valve implant, etc.) to one or more locations within the anatomy, including but not limited to, in some embodiments, the heart. In some embodiments, the medical device system 10 may include a delivery device that can be used for percutaneous delivery of a replacement heart valve implant (e.g., a replacement mitral valve, a replacement aortic valve, etc.) to an area of interest in the anatomy, such as a native heart valve. This, however, is not intended to be limiting as the medical device system 10 and/or the delivery device may also be used for other interventions including valve repair, valvuloplasty, and the like, or other similar interventions.

The medical device system 10 including a catheter 40 having a lumen 42 extending from a proximal opening to a distal opening, a core wire 30 slidably disposed within the lumen 42, and a medical implant 100 (e.g., a cardiovascular medical implant, an occlusive medical implant, a replacement heart valve implant, etc.) having an expandable framework 110 configure to shift between a collapsed configuration (e.g., FIG. 1), wherein the medical implant 100 is disposed within the lumen 42 proximate the distal opening in the collapsed configuration, and an expanded configuration (e.g., FIG. 2), wherein the medical implant 100 and/or the expandable framework 110 is configured to shift between the collapsed configuration and the expanded configuration when the medical implant 100 is disposed distal of the distal opening of the lumen 42 and/or the catheter 40, and/or when the medical implant 100 is unconstrained by the catheter 40. The medical implant 100 may be disposed at and/or releasably connected to a distal portion of the core wire 30. The core wire 30 may be slidably and/or rotatably disposed within the lumen 42 of the catheter 40. In some embodiments, a proximal end of the core wire 30 may extend proximally of a proximal end of the catheter 40 and/or the proximal opening of the lumen 42 for manual manipulation by a clinician or practitioner. In some embodiments, the example medical implant 100 may be removably attached, joined, or otherwise connected to the distal end of the core wire 30. Some suitable, but non-limiting, examples of materials for the medical device system 10, the core wire 30, the catheter 40, and/or the medical implant 100, etc. are discussed below. It is contemplated that any and/or all example occlusive implants disclosed herein may be used in accordance with and/or be associated with the example medical device system 10 described above.

Figure 3:
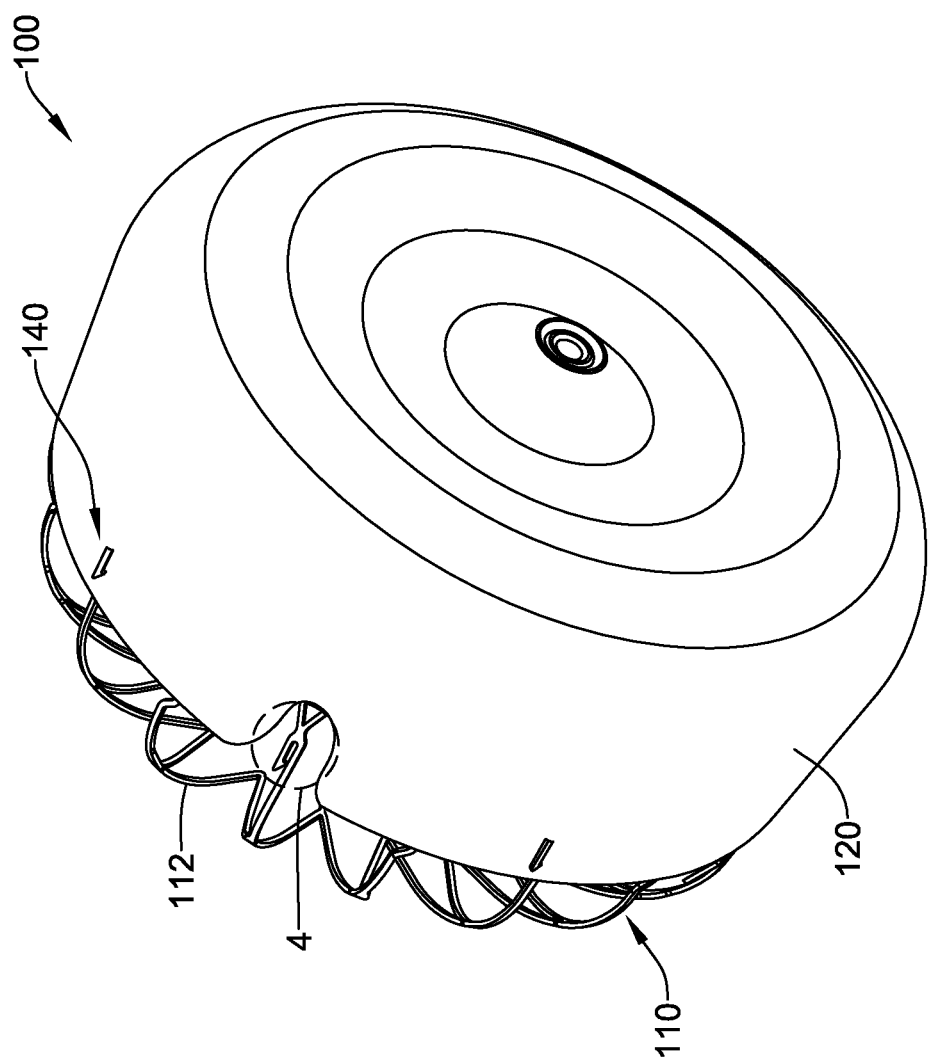
FIG. 3 is a partial cutaway view of an example medical implant.

FIG. 3 illustrates an example configuration of the medical implant 100 comprising the expandable framework 110 configured to shift between the collapsed configuration and the expanded configuration. The expandable framework 110 may comprise a plurality of interconnected struts 112 defining a plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements. The expandable framework 110 may be compliant and substantially conform to and/or be in sealing engagement with the shape and/or geometry of a lateral wall of a left atrial appendage in the expanded configuration. In some embodiments, the medical implant 100 may expand to a size, extent, or shape less than or different from a maximum unconstrained extent, as determined by the surrounding tissue and/or lateral wall of the left atrial appendage. In some embodiments, reducing a thickness of various elements of the expandable framework 110 may increase the flexibility and compliance of the expandable framework 110 and/or the medical implant 100, thereby permitting the expandable framework 110 and/or the medical implant 100 to conform to the tissue around it, rather than forcing the tissue to conform to the expandable framework 110 and/or the medical implant 100.

In some embodiments, a proximal end of the expandable framework 110 may be configured to releasably attach, join, couple, engage, or otherwise connect to the distal end of the core wire 30. In some embodiments, the proximal end of the expandable framework 110 may include a threaded insert coupled thereto. In some embodiments, the threaded insert may be configured to and/or adapted to couple with, join to, mate with, or otherwise engage a threaded member disposed at the distal end of the core wire 30. Other means of releasably coupling and/or engaging the proximal end of the expandable framework 110 to the distal end of the core wire 30 are also contemplated.

Figure 4:
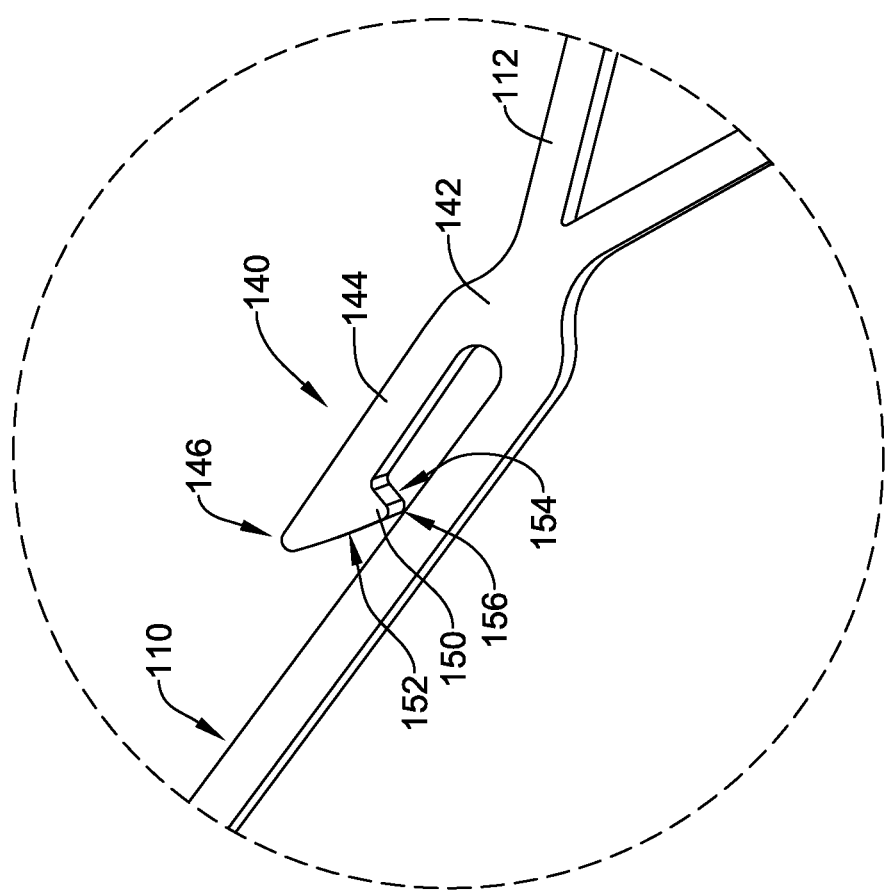
FIG. 4 is a detail view of a portion of the example medical implant of FIG. 3.

In some embodiments, the medical implant 100 and/or the expandable framework 110 may include a plurality of securement members 140 projecting from the plurality of interconnected struts 112. Each of the plurality of securement members 140 may include a base portion 142 attached to the plurality of interconnected struts 112, a tip portion 146, and a body portion 144 extending from the base portion 142 to the tip portion 146, as seen in FIG. 4 for example. In some embodiments, the tip portion 146 of each of, some of, or one of the plurality of securement members 140 may be radially aligned with the plurality of interconnected struts 112 (e.g., on a common circumference). In some embodiments, the body portion 144 and/or the tip portion 146 of the plurality of securement members 140 may be oriented substantially parallel to the plurality of interconnected struts 112. In some embodiments, the tip portion 146 of each of, some of, or one of the plurality of securement members 140 does not extend radially outward of the plurality of interconnected struts 112. As such, the plurality of securement members 140 and/or the tip portion 146 of the plurality of securement members 140 may be incapable of engaging with, extending into, and/or piercing native tissue(s) disposed outside of (e.g., radially outward of, etc.) the expandable framework 110 and/or the plurality of interconnected struts 112.

Returning to FIG. 3, in some embodiments, the medical implant 100 may include an occlusive element 120 (e.g., a membrane, a fabric, or a tissue element, etc.) connected to, disposed on, disposed over, disposed about, or covering at least a portion of the expandable framework 110 and/or the plurality of interconnected struts 112. In some embodiments, the occlusive element 120 (e.g., the membrane, the fabric, or the tissue element, etc.) may be connected to, disposed on, disposed over, disposed about, or cover at least a portion of an outer (or outwardly-facing) surface of the expandable framework 110 and/or the plurality of interconnected struts 112. In some embodiments, the occlusive element 120 (e.g., the membrane, the fabric, or the tissue element, etc.) may be connected to, disposed on, disposed over, disposed about, or covering the proximal end of the expandable framework 110.

In some embodiments, the medical implant 100 may further include a second occlusive element 120 (e.g., a second membrane, a second fabric, or a second tissue element, etc.) connected to, disposed on, disposed over, disposed about, or covering at least a portion of the expandable framework 110 and/or the plurality of interconnected struts 112. In some embodiments, the second occlusive element 120 (e.g., the second membrane, the second fabric, or the second tissue element, etc.) may be connected to, disposed on, disposed over, disposed about, or cover at least a portion of an outer (or outwardly-facing) surface of the expandable framework 110 and/or the plurality of interconnected struts 112. In some embodiments, the second occlusive element 120 (e.g., the second membrane, the second fabric, or the second tissue element, etc.) may be connected to, disposed on, disposed over, disposed about, or covering the distal end of the expandable framework 110. Some, all, or none of the features described herein with respect to the occlusive element 120 (e.g., the membrane, the fabric, or the tissue element, etc.) may also apply and/or be used with the second occlusive element 120 (e.g., the second membrane, the second fabric, or the second tissue element, etc.), including but not limited to means of attachment to the expandable framework 110 and/or the plurality of interconnected struts 112. In some embodiments, the second occlusive element 120 (e.g., the second membrane, the second fabric, or the second tissue element, etc.) can be the same material or a different material than the occlusive element 120 (e.g., the membrane, the fabric, or the tissue element, etc.).

The occlusive element 120 (e.g., the membrane, the fabric, or the tissue element, etc.) may have an inner surface and an outer surface. In some embodiments, one of the inner surface or the outer surface of the occlusive element 120 (e.g., the membrane, the fabric, or the tissue element, etc.) may face a surface of the plurality of interconnected struts 112 (e.g., an inner surface, an outer surface, etc.), and the other of the inner surface or the outer surface of the occlusive element 120 (e.g., the membrane, the fabric, or the tissue element, etc.) not facing the plurality of interconnected struts 112 may face an opposing surface of each of, some of, or one of the plurality of securement members 140. In some embodiments, one of the inner surface or the outer surface of the occlusive element 120 (e.g., the membrane, the fabric, or the tissue element, etc.) may be in contact with a surface of the plurality of interconnected struts 112 (e.g., an inner surface, an outer surface, etc.), and the other of the inner surface or the outer surface of the occlusive element 120 (e.g., the membrane, the fabric, or the tissue element, etc.) not in contact with the plurality of interconnected struts 112 may lie flush against and/or be in contact with an opposing surface of each of, some of, or one of the plurality of securement members 140. In some embodiments, one of the inner surface or the outer surface of the occlusive element 120 (e.g., the membrane, the fabric, or the tissue element, etc.) may be in contact with a surface of the plurality of interconnected struts 112 (e.g., an inner surface, an outer surface, etc.), and the other of the inner surface or the outer surface of the occlusive element 120 (e.g., the membrane, the fabric, or the tissue element, etc.) not in contact with the plurality of interconnected struts 112 may face an opposing surface of each of, some of, or one of the plurality of securement members 140.

In some embodiments, the tip portion 146 of the plurality of securement members 140 may be capable of piercing the occlusive element 120 (e.g., the membrane, the fabric, or the tissue element, etc.). In some embodiments, the occlusive element 120 (e.g., the membrane, the fabric, or the tissue element, etc.) may optionally include one or more holes or apertures configured to receive the tip portion 146 and/or the body portion 144 of each of, some of, or one of the plurality of securement members 140. Each of, some of, or one of the plurality of securement members 140 may extend through the occlusive element 120 (e.g., the membrane, the fabric, or the tissue element, etc.) at least once (e.g., from the inner surface to the outer surface, from the outer surface to the inner surface). In some embodiments, each of, some of, or one of the plurality of securement members 140 may extend through the occlusive element 120 (e.g., the membrane, the fabric, or the tissue element, etc.) two times, three times, four times, or more (e.g., from the inner surface to the outer surface, from the outer surface to the inner surface).

In some embodiments, the tip portion 146 of each of, some of, or one of the plurality of securement members 140 may extend axially toward an inflow end of the occlusive element 120 (e.g., the membrane, the fabric, or the tissue element, etc.) and/or the expandable framework 110. In some embodiments, the body portion 144 of each of, some of, or one of the plurality of securement members 140 may extend axially toward the inflow end of the occlusive element 120 (e.g., the membrane, the fabric, or the tissue element, etc.) and/or the expandable framework 110. In some embodiments, the tip portion 146 of each of, some of, or one of the plurality of securement members 140 may extend axially toward an outflow end of the occlusive element 120 (e.g., the membrane, the fabric, or the tissue element, etc.) and/or the expandable framework 110. In some embodiments, the body portion 144 of each of, some of, or one of the plurality of securement members 140 may extend axially toward the outflow end of the occlusive element 120 (e.g., the membrane, the fabric, or the tissue element, etc.) and/or the expandable framework 110.

In some embodiments, the tip portion 146 of each of, some of, or one of the plurality of securement members 140 may alternatingly extend axially toward the inflow end and the outflow end of the occlusive element 120 (e.g., the membrane, the fabric, or the tissue element, etc.) and/or the expandable framework 110. In some embodiments, the body portion 144 of each of, some of, or one of the plurality of securement members 140 may alternatingly extend axially toward the inflow end and the outflow end of the occlusive element 120 (e.g., the membrane, the fabric, or the tissue element, etc.) and/or the expandable framework 110. For example, a first securement member 140 may extend axially toward the inflow end of the occlusive element 120 (e.g., the membrane, the fabric, or the tissue element, etc.) and/or the expandable framework 110, and a second adjacent securement member 140 may extend axially toward the outflow end of the occlusive element 120 (e.g., the membrane, the fabric, or the tissue element, etc.) and/or the expandable framework 110, and so on circumferentially around and/or about the expandable framework 110.

The body portion 144 of each of the plurality of securement members 140 may be attached to the expandable framework 110 at the base portion 142 of its respective securement member 140. In one example, the tip portion 146 of each of the plurality of securement members 140 may be formed with a generally straight or spear shape such that a free end of the securement member 140 generally extends axially and/or toward the inflow end the occlusive element 120 (e.g., the membrane, the fabric, or the tissue element, etc.) and/or the expandable framework 110. In some embodiments, each of, some of, or one of the plurality of securement members 140 may include at least one barb 150 extending and/or projecting laterally and/or circumferentially from its respective securement member 140. In some embodiments, the at least one barb 150 of the plurality of securement members 140 extending and/or projecting laterally and/or circumferentially from each of, some of, or one of the plurality of securement members 140 projects from the body portion 144 and/or the tip portion 146 of its respective securement member 140. Each of the at least one barb 150 may project from the body portion 144 and/or the tip portion 146 of the plurality of securement members 140 in a circumferential direction around the expandable framework 110 and/or a central longitudinal axis of the medical implant 100. In at least some embodiments, the circumferential direction may be transverse, lateral, and/or generally perpendicular to the body portion 144 and/or the tip portion 146 of the plurality of securement members 140. Similar to above, in some embodiments, the at least one barb 150 of each of, some of, or one of the plurality of securement members 140 does not extend radially outward of the plurality of interconnected struts 112. As such, the plurality of securement members 140 and/or the at least one barb 150 of the plurality of securement members 140 may be incapable of engaging with, extending into, and/or piercing native tissue(s) disposed outside of (e.g., radially outward of, etc.) the expandable framework 110 and/or the plurality of interconnected struts 112.

Each of the at least one barb 150 of the plurality of securement members 140 may include a forward surface 152 facing towards the tip portion 146 of its respective securement member 140, and a rear surface 154 facing towards the base portion 142 and/or the body portion 144 of its respective securement member 140. The forward surface 152 may be positioned at an obtuse angle relative to the body portion 144 and/or the tip portion 146 of its respective securement member 140. For example, the forward surface 152 may face distally and/or away from the base portion 142 and/or the body portion 144, as well as circumferentially relative to the body portion 144 of its respective securement member 140 and/or the central longitudinal axis of the medical implant 100. In at least some embodiments, the rear surface 154 may be positioned at an obtuse angle relative to the body portion 144 of its respective securement member 140, and the forward surface 152 and the rear surface 154 may be angled to face in a common and/or the same circumferential direction. For example, the rear surface 154 may face proximally and/or toward the base portion 142 and/or the body portion 144, as well as circumferentially relative to the body portion 144 of its respective securement member 140 and/or the central longitudinal axis of the medical implant 100. Alternatively, in some embodiments, the rear surface 154 may be positioned at an acute angle or a right angle relative to the body portion 144 of its respective securement member 140, and in embodiments with the acute angle, the forward surface 152 and the rear surface 154 may be angled to face in opposing circumferential directions. An intersection of the forward surface 152 with the rear surface 154 may form a barb tip 156. In at least some embodiments, the barb tip 156 may be rounded. For example, the barb tip 156 may be formed with a radius of about 0.025 inches (0.635 mm), 0.015 inches (0.381 mm), 0.010 inches (0.254 mm), 0.005 inches (0.127 mm), 0.002 inches (0.0508 mm), 0.001 inches (0.0254 mm), or another suitable dimension as desired. Additional and/or other configurations are also contemplated, at least some of which are described herein.

In some embodiments, the occlusive element 120 (e.g., the membrane, the fabric, or the tissue element, etc.) may extend distally past at least some of the plurality of securement members 140. In some embodiments, the occlusive element 120 (e.g., the membrane, the fabric, or the tissue element, etc.) may extend distally past each and/or all of the plurality of securement members 140.

In some embodiments, the at least one barb 150 on each of, some of, or one of the plurality of securement members 140 may be disposed radially outward of the occlusive element 120 (e.g., the membrane, the fabric, or the tissue element, etc.) and/or the outer surface of the occlusive element 120 (e.g., the membrane, the fabric, or the tissue element, etc.) while the base portion 142 of its respective securement member 140 is disposed radially inward of the occlusive element 120 (e.g., the membrane, the fabric, or the tissue element, etc.) and/or the inner surface of the occlusive element 120 (e.g., the membrane, the fabric, or the tissue element, etc.). The at least one barb 150 may serve to retain the occlusive element 120 (e.g., the membrane, the fabric, or the tissue element, etc.) on the expandable framework 110 and/or the plurality of securement members 140, thereby preventing the occlusive element 120 (e.g., the membrane, the fabric, or the tissue element, etc.) from working loose and/or releasing from the expandable framework 110 as the expandable framework 110 is shifted between the collapsed configuration and the expanded configuration. In some embodiments, attachment of the occlusive element 120 (e.g., the membrane, the fabric, or the tissue element, etc.) to the expandable framework 110 may be substantially devoid of sutures and/or adhesives.

In some embodiments, the occlusive element 120 (e.g., the membrane, the fabric, or the tissue element, etc.) may be permeable or impermeable to blood and/or other fluids, such as water. In some embodiments, the occlusive element 120 (e.g., the membrane, the fabric, or the tissue element, etc.) may include a polymeric membrane, a metallic or polymeric mesh, a porous or semi-porous filter-like material, or other suitable construction. In some embodiments, the occlusive element 120 (e.g., the membrane, the fabric, or the tissue element, etc.) prevents thrombi (e.g., blood clots, etc.) from passing through the occlusive element 120 (e.g., the membrane, the fabric, or the tissue element, etc.) and out of the left atrial appendage into the blood stream. In some embodiments, the occlusive element 120 (e.g., the membrane, the fabric, or the tissue element, etc.) promotes endothelization after implantation, thereby effectively removing the target site (e.g., the left atrial appendage, etc.) from the patient's circulatory system. Some suitable, but non-limiting, examples of materials for the occlusive element 120 (e.g., the membrane, the fabric, or the tissue element, etc.) are discussed below.

In some embodiments, the expandable framework 110, the plurality of interconnected struts 112, and/or the plurality of securement members 140 may be integrally formed and/or cut from a unitary member. In some embodiments, the expandable framework 110, the plurality of interconnected struts 112, and/or the plurality of securement members 140 may be integrally formed and/or cut from a unitary tubular member and subsequently formed and/or heat set to a desired shape in the expanded configuration. In some embodiments, the expandable framework 110, the plurality of interconnected struts 112, and/or the plurality of securement members 140 may be integrally formed and/or cut from a unitary flat member or sheet, and then rolled or formed into a tubular structure and subsequently formed and/or heat set to the desired shape in the expanded configuration. Some exemplary means and/or methods of making and/or forming the expandable framework 110 include laser cutting, machining, punching, stamping, electro discharge machining (EDM), chemical dissolution, etc. Other means and/or methods are also contemplated.

In some embodiments, the expandable framework 110 may include a plurality of anchor members disposed about a periphery of the expandable framework 110 in the expanded configuration. The plurality of anchor members may extend radially outward from the expandable framework 110. In some embodiments, at least some of the plurality of anchor members may each have and/or include a body portion and a tip portion, and in some instances, a barb projecting outward from the body portion and/or the tip portion. In some embodiments, the plurality of anchor members may provide an anchoring mechanism to aid in retaining the medical implant 100 at a target site within a patient's anatomy (e.g., the left atrial appendage, for example) in the expanded configuration. In some embodiments, the barb(s) may be configured, positioned, and/or arranged to engage with native tissue at the target site to enhance anchoring of the medical implant 100 and/or the expandable framework 110 at the target site. For example, the barb(s) may puncture, pierce, and/or extend into the surrounding tissue in the expanded configuration. In some embodiments, the barb(s) may be configured, positioned, and/or arranged such that engagement of the barb(s) with native tissue at the target site is minimized or avoided so as to limit irritation or injury to the native tissue and/or to easier facilitate removal or repositioning of the medical implant 100 and/or the expandable framework 110. For example, the barb(s) may not puncture, pierce, and/or extend into the surrounding tissue in the expanded configuration.

Figure 5:
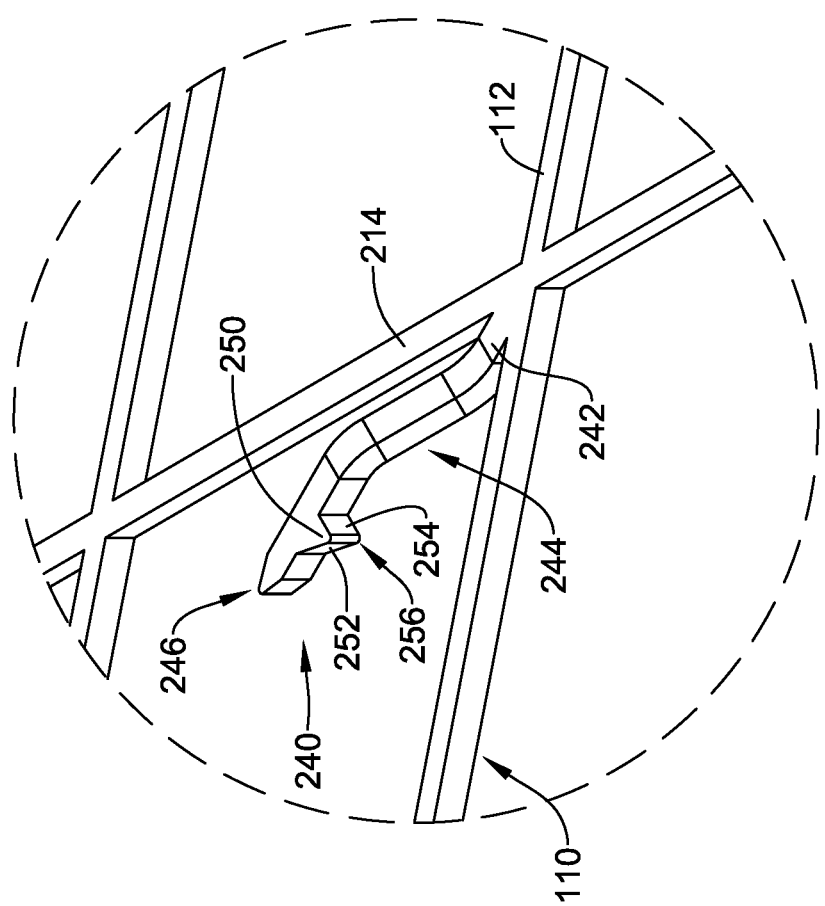
FIGS. 5 and 6 illustrate a portion of the example medical implant of FIG. 3 in an alternative configuration.
Figure 6:
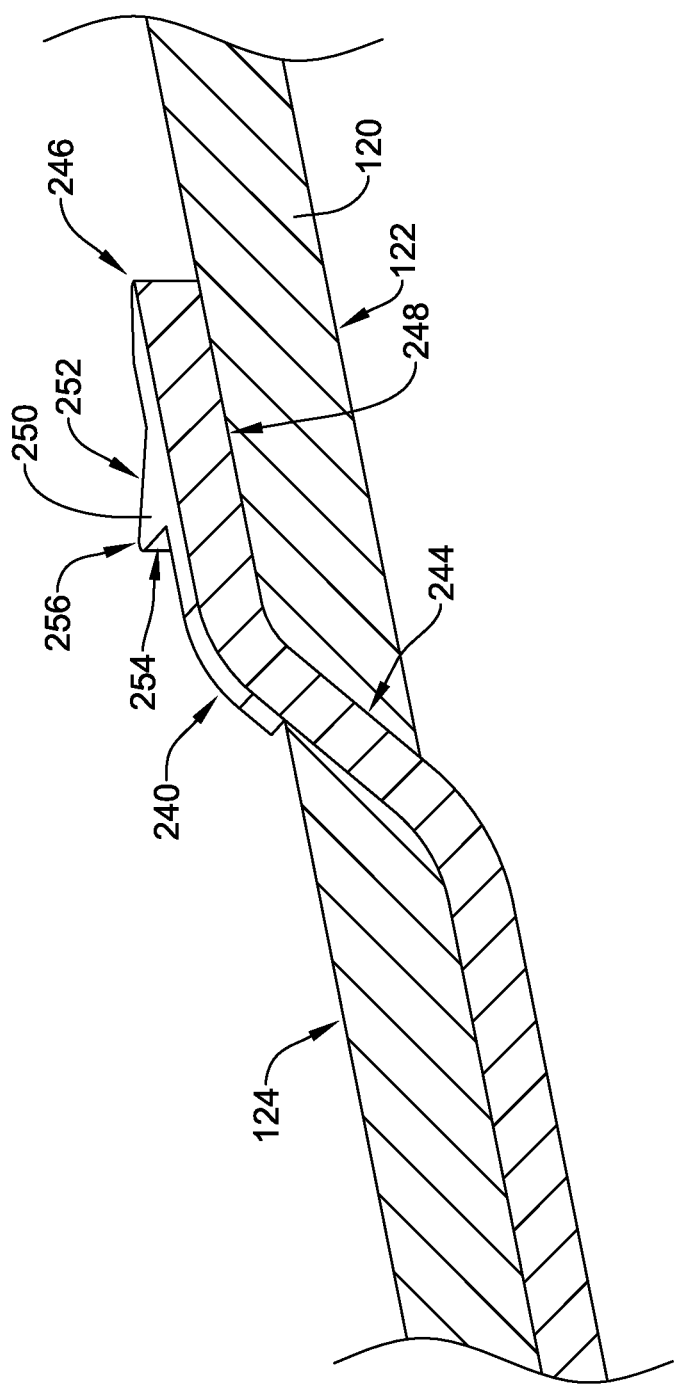

FIGS. 5 and 6 illustrate an alternative configuration of a plurality of securement members 240. In some embodiments, the plurality of securement members 240 may include a base portion 242, a body portion 244, and a tip portion 246, similar to those described above with respect to the plurality of securement members 140. The base portion 242 may be attached to the plurality of interconnected struts 112 and the body portion 244 may extend from the base portion 242 to the tip portion 246, as seen in FIG. 5 for example. In some embodiments, the tip portion 246 of each of, some of, or one of the plurality of securement members 240 may be radially offset from the plurality of interconnected struts 112. In some embodiments, the body portion 244 and/or the tip portion 246 of each of, some of, or one of the plurality of securement members 240 may be oriented substantially parallel to the plurality of interconnected struts 112. In some embodiments, the body portion 244 of each of, some of, or one of the plurality of securement members 240 may having an offset extending radially outward of the plurality of interconnected struts 112. In some embodiments, the occlusive element 120 (e.g., the membrane, the fabric, or the tissue element, etc.) may be disposed radially inward of the offset and/or the tip portion 246 of each of, some of, or one of the plurality of securement members 240.

As above, the occlusive element 120 (e.g., the membrane, the fabric, or the tissue element, etc.) may have an inner surface 122 and an outer surface 124. In some embodiments, the inner surface 122 of the occlusive element 120 (e.g., the membrane, the fabric, or the tissue element, etc.) may face towards an outer surface 214 of the plurality of interconnected struts 112 (e.g., an inner surface, an outer surface, etc.), and the outer surface 124 of the occlusive element 120 (e.g., the membrane, the fabric, or the tissue element, etc.) may face towards an inner surface 248 of each of, some of, or one of the plurality of securement members 240 and/or the offset. In some embodiments, the inner surface 122 of the occlusive element 120 (e.g., the membrane, the fabric, or the tissue element, etc.) may be in contact with the outer surface 214 of the plurality of interconnected struts 112 (e.g., an inner surface, an outer surface, etc.), and the outer surface 124 of the occlusive element 120 (e.g., the membrane, the fabric, or the tissue element, etc.) may lie flush against and/or be in contact with the inner surface 248 of each of, some of, or one of the plurality of securement members 240 and/or the offset. In some embodiments, the inner surface 122 of the occlusive element 120 (e.g., the membrane, the fabric, or the tissue element, etc.) may be in contact with the outer surface 214 of the plurality of interconnected struts 112 (e.g., an inner surface, an outer surface, etc.), and the outer surface 124 of the occlusive element 120 (e.g., the membrane, the fabric, or the tissue element, etc.) may face the inner surface 248 of each of, some of, or one of the plurality of securement members 240 and/or the offset.

In some embodiments, the tip portion 246 of the plurality of securement members 240 may be capable of piercing the occlusive element 120 (e.g., the membrane, the fabric, or the tissue element, etc.). In some embodiments, the occlusive element 120 (e.g., the membrane, the fabric, or the tissue element, etc.) may optionally include one or more holes or apertures configured to receive the tip portion 246 and/or the body portion 244 of each of, some of, or one of the plurality of securement members 240. Each of, some of, or one of the plurality of securement members 240 may extend through the occlusive element 120 (e.g., the membrane, the fabric, or the tissue element, etc.) at least once (e.g., from the inner surface to the outer surface, etc.). In some embodiments, each of, some of, or one of the plurality of securement members 240 may extend through the occlusive element 120 (e.g., the membrane, the fabric, or the tissue element, etc.) two times, three times, four times, or more (e.g., from the inner surface to the outer surface, etc.).

In some embodiments, the tip portion 246 of each of, some of, or one of the plurality of securement members 240 may extend axially toward the inflow end of the occlusive element 120 (e.g., the membrane, the fabric, or the tissue element, etc.) and/or the expandable framework 110. In some embodiments, the body portion 244 of each of, some of, or one of the plurality of securement members 240 may extend axially toward the inflow end of the occlusive element 120 (e.g., the membrane, the fabric, or the tissue element, etc.) and/or the expandable framework 110. In some embodiments, the tip portion 246 of each of, some of, or one of the plurality of securement members 240 may extend axially toward the outflow end of the occlusive element 120 (e.g., the membrane, the fabric, or the tissue element, etc.) and/or the expandable framework 110. In some embodiments, the body portion 244 of each of, some of, or one of the plurality of securement members 240 may extend axially toward the outflow end of the occlusive element 120 (e.g., the membrane, the fabric, or the tissue element, etc.) and/or the expandable framework 110.

In some embodiments, the tip portion 246 of each of, some of, or one of the plurality of securement members 240 may alternatingly extend axially toward the inflow end and the outflow end of the occlusive element 120 (e.g., the membrane, the fabric, or the tissue element, etc.) and/or the expandable framework 110. In some embodiments, the body portion 244 of each of, some of, or one of the plurality of securement members 240 may alternatingly extend axially toward the inflow end and the outflow end of the occlusive element 120 (e.g., the membrane, the fabric, or the tissue element, etc.) and/or the expandable framework 110. For example, a first securement member 240 may extend axially toward the inflow end of the occlusive element 120 (e.g., the membrane, the fabric, or the tissue element, etc.) and/or the expandable framework 110, and a second adjacent securement member 240 may extend axially toward the outflow end of the occlusive element 120 (e.g., the membrane, the fabric, or the tissue element, etc.) and/or the expandable framework 110, and so on circumferentially around and/or about the expandable framework 110.

The body portion 244 of each of the plurality of securement members 240 may be attached to the expandable framework 110 at the base portion 242 of its respective securement member 240. In one example, the tip portion 246 of each of the plurality of securement members 240 may be formed with a generally straight or spear shape such that a free end of the securement member 240 generally extends axially and/or toward the inflow end the occlusive element 120 (e.g., the membrane, the fabric, or the tissue element, etc.) and/or the expandable framework 110. Other orientations are also contemplated as discussed herein.

In some embodiments, each of, some of, or one of the plurality of securement members 240 may include at least one barb 250 extending and/or projecting laterally and/or circumferentially from its respective securement member 240. In some embodiments, the at least one barb 250 of the plurality of securement members 240 extending and/or projecting laterally and/or circumferentially from each of, some of, or one of the plurality of securement members 240 projects from the body portion 244 and/or the tip portion 246 of its respective securement member 240. Each of the at least one barb 250 may project from the body portion 244 and/or the tip portion 246 of the plurality of securement members 240 in a circumferential direction around the expandable framework 110 and/or a central longitudinal axis of the medical implant 100. In at least some embodiments, the circumferential direction may be transverse, lateral, and/or generally perpendicular to the body portion 244 and/or the tip portion 246 of the plurality of securement members 240. In some embodiments, the plurality of securement members 240 and/or the at least one barb 250 of the plurality of securement members 240 may be oriented such that the plurality of securement members 240 and/or the at least one barb 250 is incapable of engaging with, extending into, and/or piercing native tissue(s) disposed outside of (e.g., radially outward of, etc.) the expandable framework 110 and/or the plurality of interconnected struts 112.

Each of the at least one barb 250 of the plurality of securement members 240 may include a forward surface 252 facing towards the tip portion 246 of its respective securement member 240, and a rear surface 254 facing towards the base portion 242 and/or the body portion 244 of its respective securement member 240. The forward surface 252 may be positioned at an obtuse angle relative to the body portion 244 and/or the tip portion 246 of its respective securement member 240. For example, the forward surface 252 may face distally and/or away from the base portion 242 and/or the body portion 244, as well as circumferentially relative to the body portion 244 of its respective securement member 240 and/or the central longitudinal axis of the medical implant 100. In at least some embodiments, the rear surface 254 may be positioned at an obtuse angle relative to the body portion 244 of its respective securement member 240, and the forward surface 252 and the rear surface 254 may be angled to face in a common and/or the same circumferential direction. For example, the rear surface 254 may face proximally and/or toward the base portion 242 and/or the body portion 244, as well as circumferentially relative to the body portion 244 of its respective securement member 240 and/or the central longitudinal axis of the medical implant 100. Alternatively, in some embodiments, the rear surface 254 may be positioned at an acute angle or a right angle relative to the body portion 244 of its respective securement member 240, and in embodiments with the acute angle, the forward surface 252 and the rear surface 254 may be angled to face in opposing circumferential directions. An intersection of the forward surface 252 with the rear surface 254 may form a barb tip 256. In at least some embodiments, the barb tip 256 may be rounded. For example, the barb tip 256 may be formed with a radius of about 0.025 inches (0.635 mm), 0.015 inches (0.381 mm), 0.010 inches (0.254 mm), 0.005 inches (0.127 mm), 0.002 inches (0.0508 mm), 0.001 inches (0.0254 mm), or another suitable dimension as desired. Additional and/or other configurations are also contemplated, at least some of which are described herein.

In some embodiments, the occlusive element 120 (e.g., the membrane, the fabric, or the tissue element, etc.) may extend distally past at least some of the plurality of securement members 240. In some embodiments, the occlusive element 120 (e.g., the membrane, the fabric, or the tissue element, etc.) may extend distally past each and/or all of the plurality of securement members 240.

In some embodiments, the at least one barb 250 on each of, some of, or one of the plurality of securement members 240 may be disposed radially outward of the occlusive element 120 (e.g., the membrane, the fabric, or the tissue element, etc.) and/or the outer surface 124 of the occlusive element 120 (e.g., the membrane, the fabric, or the tissue element, etc.) while the base portion 242 of its respective securement member 240 is disposed radially inward of the occlusive element 120 (e.g., the membrane, the fabric, or the tissue element, etc.) and/or the inner surface 122 of the occlusive element 120 (e.g., the membrane, the fabric, or the tissue element, etc.). The at least one barb 250 may serve to retain the occlusive element 120 (e.g., the membrane, the fabric, or the tissue element, etc.) on the expandable framework 110 and/or the plurality of securement members 240, thereby preventing the occlusive element 120 (e.g., the membrane, the fabric, or the tissue element, etc.) from working loose and/or releasing from the expandable framework 110 as the expandable framework 110 is shifted between the collapsed configuration and the expanded configuration. In some embodiments, attachment of the occlusive element 120 (e.g., the membrane, the fabric, or the tissue element, etc.) to the expandable framework 110 may be substantially devoid of sutures and/or adhesives.

Figure 7:
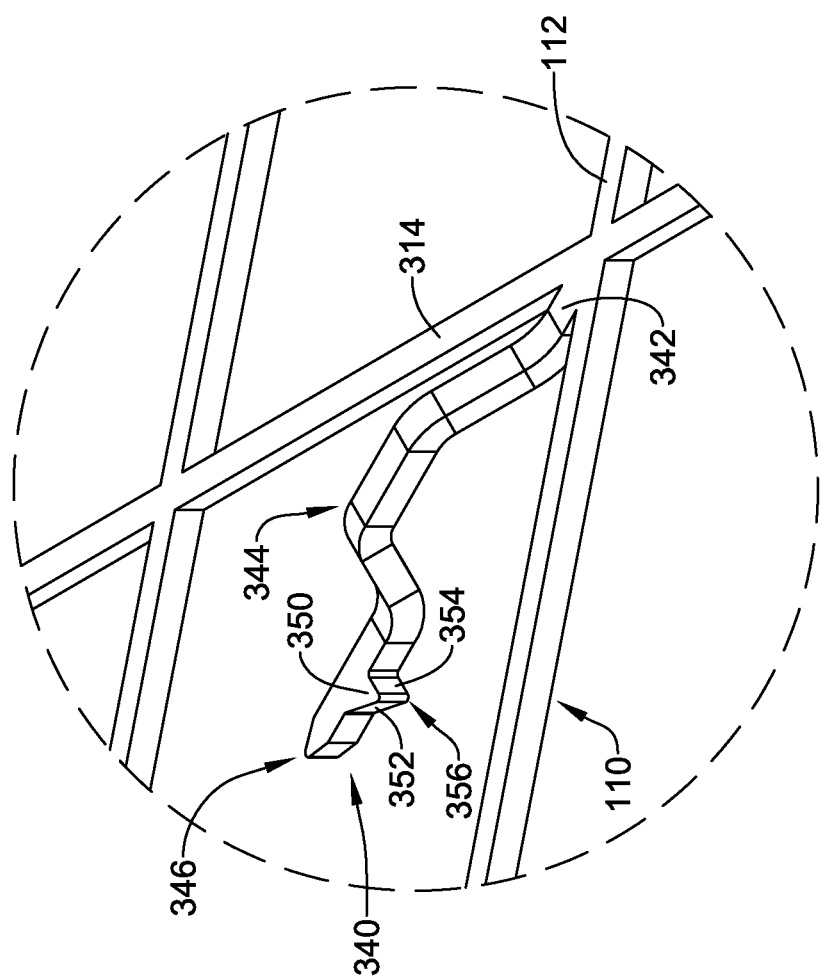
FIGS. 7 and 8 illustrate a portion of the example medical implant of FIG. 3 in an alternative configuration.
Figure 8:
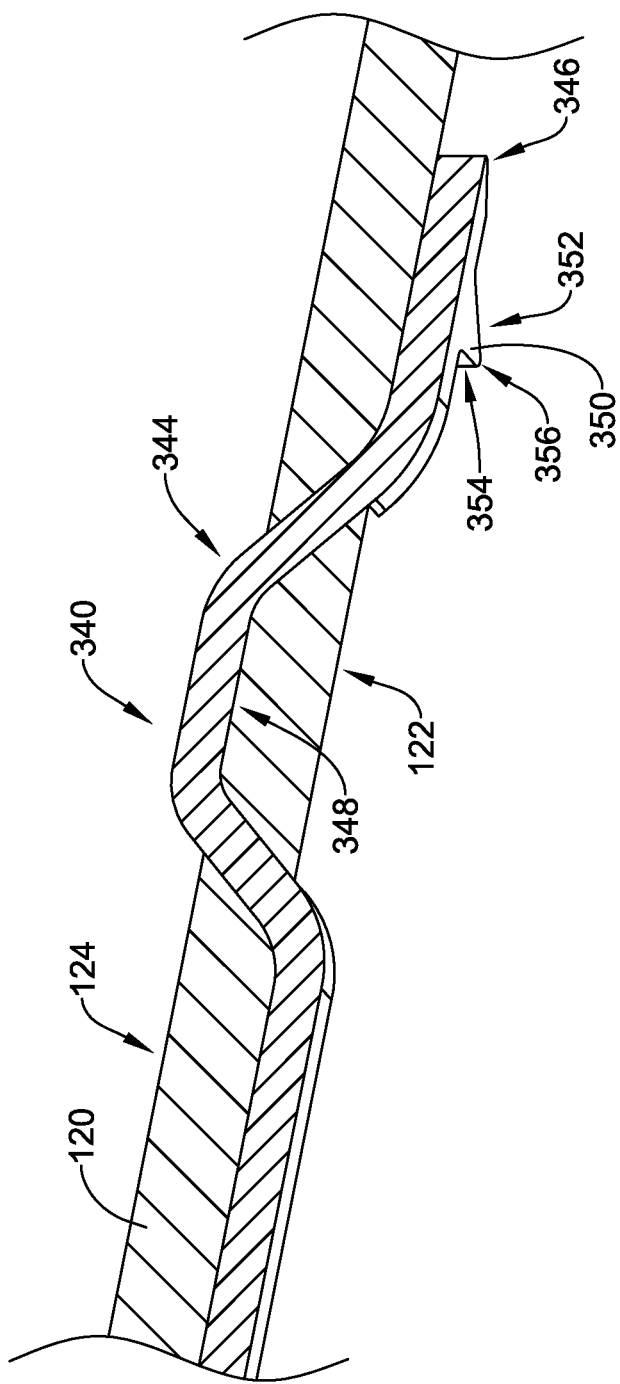

FIGS. 7 and 8 illustrate an alternative configuration of a plurality of securement members 340. In some embodiments, the plurality of securement members 340 may include a base portion 342, a body portion 344, and a tip portion 346, similar to those described above with respect to the plurality of securement members 140. The base portion 342 may be attached to the plurality of interconnected struts 112 and the body portion 344 may extend from the base portion 342 to the tip portion 346, as seen in FIG. 7 for example. In some embodiments, the tip portion 346 of each of, some of, or one of the plurality of securement members 340 may be radially aligned with the plurality of interconnected struts 112 (e.g., on a common circumference). In some embodiments, the body portion 344 and/or the tip portion 346 of each of, some of, or one of the plurality of securement members 340 may be oriented substantially parallel to the plurality of interconnected struts 112. In some embodiments, the body portion 344 of each of, some of, or one of the plurality of securement members 340 may having an offset extending radially outward of the plurality of interconnected struts 112. In some embodiments, the occlusive element 120 (e.g., the membrane, the fabric, or the tissue element, etc.) may be disposed radially inward of the offset and/or the body portion 344 of each of, some of, or one of the plurality of securement members 340. In some embodiments, the offset may comprise a double offset, wherein the body portion 344 shifts radially outward relative to the plurality of interconnected struts 112 and then shifts again radially inward relative to the plurality of interconnected struts 112, such that the body portion 344 is radially offset from the plurality of interconnected struts 112 and the tip portion 346 is radially aligned with the plurality of interconnected struts 112 (e.g., on a common circumference). In some embodiments, the tip portion 346 of each of, some of, or one of the plurality of securement members 340 does not extend radially outward of the plurality of interconnected struts 112. As such, the plurality of securement members 340 and/or the tip portion 346 of the plurality of securement members 340 may be incapable of engaging with, extending into, and/or piercing native tissue(s) disposed outside of (e.g., radially outward of, etc.) the expandable framework 110 and/or the plurality of interconnected struts 112.

As above, the occlusive element 120 (e.g., the membrane, the fabric, or the tissue element, etc.) may have an inner surface 122 and an outer surface 124. In some embodiments, one of the inner surface 122 or the outer surface 124 of the occlusive element 120 (e.g., the membrane, the fabric, or the tissue element, etc.) may face towards a surface (e.g., an inner surface, an outer surface 314, etc.) of the plurality of interconnected struts 112, and the other of the inner surface 122 or the outer surface 124 of the occlusive element 120 (e.g., the membrane, the fabric, or the tissue element, etc.) not facing the plurality of interconnected struts 112 may face towards an opposing surface (e.g., an inner surface 348, an outer surface, etc.) of each of, some of, or one of the plurality of securement members 340 and/or the offset. In some embodiments, one of the inner surface 122 or the outer surface 124 of the occlusive element 120 (e.g., the membrane, the fabric, or the tissue element, etc.) may be in contact with a surface (e.g., the inner surface, the outer surface 314, etc.) of the plurality of interconnected struts 112, and the other of the inner surface 122 or the outer surface 124 of the occlusive element 120 (e.g., the membrane, the fabric, or the tissue element, etc.) not in contact with the plurality of interconnected struts 112 may lie flush against and/or be in contact with an opposing surface (e.g., the inner surface 348, the outer surface, etc.) of each of, some of, or one of the plurality of securement members 340 and/or the offset. In some embodiments, one of the inner surface 122 or the outer surface 124 of the occlusive element 120 (e.g., the membrane, the fabric, or the tissue element, etc.) may be in contact with a surface (e.g., the inner surface, the outer surface 314, etc.) of the plurality of interconnected struts 112, and the other of the inner surface 122 or the outer surface 124 of the occlusive element 120 (e.g., the membrane, the fabric, or the tissue element, etc.) not in contact with the plurality of interconnected struts 112 may face an opposing surface (e.g., the inner surface 348, the outer surface, etc.) of each of, some of, or one of the plurality of securement members 340 and/or the offset. In some embodiments, one of the inner surface 122 or the outer surface 124 of the occlusive element 120 (e.g., the membrane, the fabric, or the tissue element, etc.) may be in contact with a surface (e.g., the inner surface, the outer surface 314, etc.) of the plurality of interconnected struts 112, and the other of the inner surface 122 or the outer surface 124 of the occlusive element 120 (e.g., the membrane, the fabric, or the tissue element, etc.) not in contact with the plurality of interconnected struts 112 may lie flush against an opposing surface (e.g., the inner surface 348, the outer surface, etc.) of each of, some of, or one of the plurality of securement members 340 and/or the offset.

In some embodiments, the tip portion 346 of the plurality of securement members 340 may be capable of piercing the occlusive element 120 (e.g., the membrane, the fabric, or the tissue element, etc.). In some embodiments, the occlusive element 120 (e.g., the membrane, the fabric, or the tissue element, etc.) may optionally include one or more holes or apertures configured to receive the tip portion 346 and/or the body portion 344 of each of, some of, or one of the plurality of securement members 340. Each of, some of, or one of the plurality of securement members 340 may extend through the occlusive element 120 (e.g., the membrane, the fabric, or the tissue element, etc.) at least once (e.g., from the inner surface to the outer surface, etc.). In some embodiments, each of, some of, or one of the plurality of securement members 340 may extend through the occlusive element 120 (e.g., the membrane, the fabric, or the tissue element, etc.) two times, three times, four times, or more (e.g., from the inner surface to the outer surface, etc.). In some embodiments, the occlusive element 120 (e.g., the membrane, the fabric, or the tissue element, etc.) may be disposed radially inward of the offset and/or the body portion 344 of each of, some of, or one of the plurality of securement members 340.

In some embodiments, the tip portion 346 of each of, some of, or one of the plurality of securement members 340 may extend axially toward the inflow end of the occlusive element 120 (e.g., the membrane, the fabric, or the tissue element, etc.) and/or the expandable framework 110. In some embodiments, the body portion 344 of each of, some of, or one of the plurality of securement members 340 may extend axially toward the inflow end of the occlusive element 120 (e.g., the membrane, the fabric, or the tissue element, etc.) and/or the expandable framework 110. In some embodiments, the tip portion 346 of each of, some of, or one of the plurality of securement members 340 may extend axially toward the outflow end of the occlusive element 120 (e.g., the membrane, the fabric, or the tissue element, etc.) and/or the expandable framework 110. In some embodiments, the body portion 344 of each of, some of, or one of the plurality of securement members 340 may extend axially toward the outflow end of the occlusive element 120 (e.g., the membrane, the fabric, or the tissue element, etc.) and/or the expandable framework 110.

In some embodiments, the tip portion 346 of each of, some of, or one of the plurality of securement members 340 may alternatingly extend axially toward the inflow end and the outflow end of the occlusive element 120 (e.g., the membrane, the fabric, or the tissue element, etc.) and/or the expandable framework 110. In some embodiments, the body portion 344 of each of, some of, or one of the plurality of securement members 340 may alternatingly extend axially toward the inflow end and the outflow end of the occlusive element 120 (e.g., the membrane, the fabric, or the tissue element, etc.) and/or the expandable framework 110. For example, a first securement member 340 may extend axially toward the inflow end of the occlusive element 120 (e.g., the membrane, the fabric, or the tissue element, etc.) and/or the expandable framework 110, and a second adjacent securement member 340 may extend axially toward the outflow end of the occlusive element 120 (e.g., the membrane, the fabric, or the tissue element, etc.) and/or the expandable framework 110, and so on circumferentially around and/or about the expandable framework 110.

The body portion 344 of each of the plurality of securement members 340 may be attached to the expandable framework 110 at the base portion 342 of its respective securement member 340. In one example, the tip portion 346 of each of the plurality of securement members 340 may be formed with a generally straight or spear shape such that a free end of the securement member 340 generally extends axially and/or toward the inflow end the occlusive element 120 (e.g., the membrane, the fabric, or the tissue element, etc.) and/or the expandable framework 110. Other orientations are also contemplated as discussed herein.

In some embodiments, each of, some of, or one of the plurality of securement members 340 may include at least one barb 350 extending and/or projecting laterally and/or circumferentially from its respective securement member 340. In some embodiments, the at least one barb 350 of the plurality of securement members 340 extending and/or projecting laterally and/or circumferentially from each of, some of, or one of the plurality of securement members 340 projects from the body portion 344 and/or the tip portion 346 of its respective securement member 340. Each of the at least one barb 350 may project from the body portion 344 and/or the tip portion 346 of the plurality of securement members 340 in a circumferential direction around the expandable framework 110 and/or a central longitudinal axis of the medical implant 100. In at least some embodiments, the circumferential direction may be transverse, lateral, and/or generally perpendicular to the body portion 344 and/or the tip portion 346 of the plurality of securement members 340.

Each of the at least one barb 350 of the plurality of securement members 340 may include a forward surface 352 facing towards the tip portion 346 of its respective securement member 340, and a rear surface 354 facing towards the base portion 342 and/or the body portion 344 of its respective securement member 340. The forward surface 352 may be positioned at an obtuse angle relative to the body portion 344 and/or the tip portion 346 of its respective securement member 340. For example, the forward surface 352 may face distally and/or away from the base portion 342 and/or the body portion 344, as well as circumferentially relative to the body portion 344 of its respective securement member 340 and/or the central longitudinal axis of the medical implant 100. In at least some embodiments, the rear surface 354 may be positioned at an obtuse angle relative to the body portion 344 of its respective securement member 340, and the forward surface 352 and the rear surface 354 may be angled to face in a common and/or the same circumferential direction. For example, the rear surface 354 may face proximally and/or toward the base portion 342 and/or the body portion 344, as well as circumferentially relative to the body portion 344 of its respective securement member 340 and/or the central longitudinal axis of the medical implant 100. Alternatively, in some embodiments, the rear surface 354 may be positioned at an acute angle or a right angle relative to the body portion 344 of its respective securement member 340, and in embodiments with the acute angle, the forward surface 352 and the rear surface 354 may be angled to face in opposing circumferential directions. An intersection of the forward surface 352 with the rear surface 354 may form a barb tip 356. In at least some embodiments, the barb tip 356 may be rounded. For example, the barb tip 356 may be formed with a radius of about 0.025 inches (0.635 mm), 0.015 inches (0.381 mm), 0.010 inches (0.254 mm), 0.005 inches (0.127 mm), 0.002 inches (0.0508 mm), 0.001 inches (0.0254 mm), or another suitable dimension as desired. Additional and/or other configurations are also contemplated, at least some of which are described herein.

In some embodiments, the occlusive element 120 (e.g., the membrane, the fabric, or the tissue element, etc.) may extend distally past at least some of the plurality of securement members 340. In some embodiments, the occlusive element 120 (e.g., the membrane, the fabric, or the tissue element, etc.) may extend distally past each and/or all of the plurality of securement members 340.

In some embodiments, the at least one barb 350 on each of, some of, or one of the plurality of securement members 340 may be disposed radially outward of the occlusive element 120 (e.g., the membrane, the fabric, or the tissue element, etc.) and/or the outer surface 124 of the occlusive element 120 (e.g., the membrane, the fabric, or the tissue element, etc.) while the base portion 342 of its respective securement member 340 is disposed radially inward of the occlusive element 120 (e.g., the membrane, the fabric, or the tissue element, etc.) and/or the inner surface 122 of the occlusive element 120 (e.g., the membrane, the fabric, or the tissue element, etc.). The at least one barb 350 may serve to retain the occlusive element 120 (e.g., the membrane, the fabric, or the tissue element, etc.) on the expandable framework 110 and/or the plurality of securement members 340, thereby preventing the occlusive element 120 (e.g., the membrane, the fabric, or the tissue element, etc.) from working loose and/or releasing from the expandable framework 110 as the expandable framework 110 is shifted between the collapsed configuration and the expanded configuration. In some embodiments, attachment of the occlusive element 120 (e.g., the membrane, the fabric, or the tissue element, etc.) to the expandable framework 110 may be substantially devoid of sutures and/or adhesives.

Figure 9:
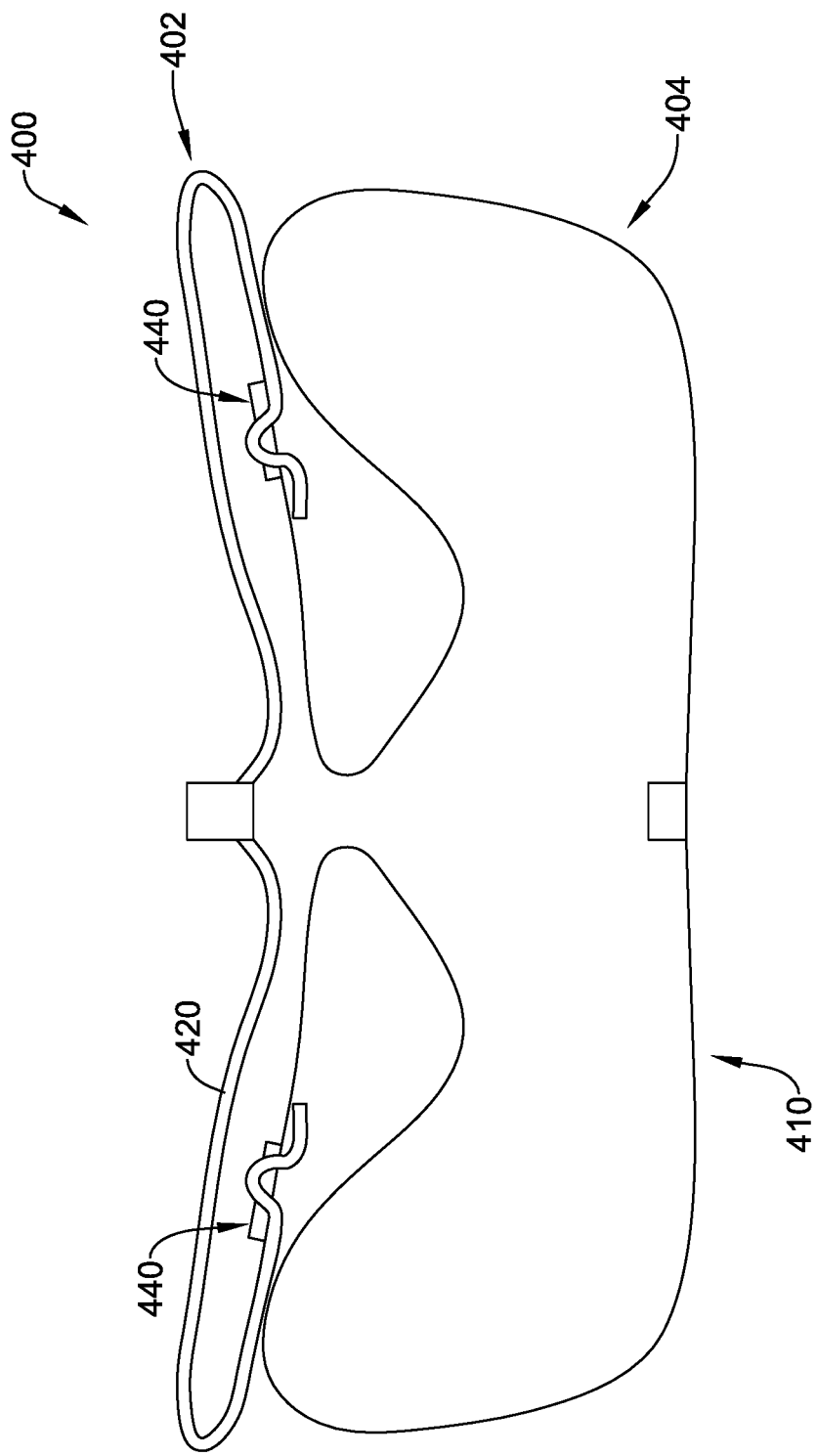
FIG. 9 schematically illustrates an alternative medical implant.

FIG. 9 illustrates a partial cross-section of an alternative medical implant 400 that may benefit from use of the disclosed securement member(s). In one example, the medical implant 400 may be an occlusive device for use in the left atrial appendage. In some embodiments, the medical implant 400 may include an expandable framework 410 configured to shift between a collapsed configuration and an expanded configuration, wherein the expandable framework 410 may comprise a plurality of interconnected struts defining a plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements. In some embodiments, the medical implant 400 and/or the expandable framework 410 may include a proximal disc portion 402 and a distal body portion 404 in the expanded configuration.

The medical implant 400 may include an occlusive element 420 (e.g., a membrane, a fabric, or a tissue element, etc.) connected to, disposed on, disposed over, disposed about, or covering at least a portion of the expandable framework 410 and/or the plurality of interconnected struts. In some embodiments, the occlusive element 420 (e.g., the membrane, the fabric, or the tissue element, etc.) may be connected to, disposed on, disposed over, disposed about, or cover at least a portion of an outer (or outwardly-facing) surface of the expandable framework 410 and/or the plurality of interconnected struts. In some embodiments, the occlusive element 420 (e.g., the membrane, the fabric, or the tissue element, etc.) may be connected to, disposed on, disposed over, disposed about, or covering the proximal disc portion 402 of the expandable framework 410.

Figure 10:
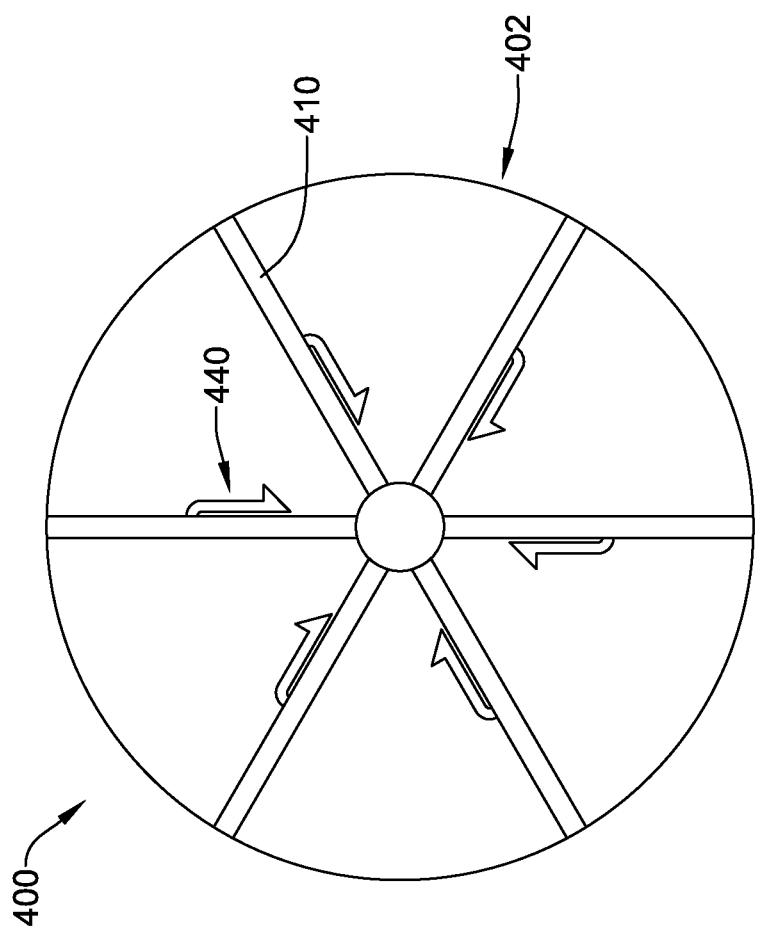
FIG. 10 illustrates a top view of a portion of the alternative medical implant of FIG. 9.

In some embodiments, the medical implant 400 and/or the expandable framework 410 may include a plurality of securement members 440 projecting from the plurality of interconnected struts. In some embodiments, the proximal disc portion 402 of the expandable framework 410 may include the plurality of securement members 440 projecting from the plurality of interconnected struts. Each of the plurality of securement members 440 may include a base portion attached to the plurality of interconnected struts, a tip portion, and a body portion extending from the base portion to the tip portion and may be formed similar to the securement members discussed herein. In some embodiments, the tip portion of each of, some of, or one of the plurality of securement members 440 may be aligned with at least some of and/or at least a portion of the plurality of interconnected struts. In some embodiments, the body portion and/or the tip portion of the plurality of securement members may be radially-oriented relative to a central longitudinal axis of the medical implant 400 and/or the expandable framework 410, as seen in FIG. 10 for example.

In some embodiments the tip portion may extend radially inward from the base portion and/or the body portion. In some embodiments, the tip portion of each of, some of, or one of the plurality of securement members 440 does not extend at a skewed angle relative to the plurality of interconnected struts. In some embodiments, the tip portion of each of, some of, or one of the plurality of securement members 440 may not extend outside of a perimeter defined by the expandable framework 410 and/or the plurality of interconnected struts. As such, the plurality of securement members 440 and/or the tip portion of the plurality of securement members 440 may be incapable of engaging with, extending into, and/or piercing native tissue(s) disposed outside of the expandable framework 410 and/or the plurality of interconnected struts.

The occlusive element 420 (e.g., the membrane, the fabric, or the tissue element, etc.) may have an inner surface and an outer surface. In some embodiments, one of the inner surface or the outer surface of the occlusive element 420 (e.g., the membrane, the fabric, or the tissue element, etc.) may face a surface of the plurality of interconnected struts (e.g., an inner surface, an outer surface, etc.), and the other of the inner surface or the outer surface of the occlusive element 420 (e.g., the membrane, the fabric, or the tissue element, etc.) not facing the plurality of interconnected struts may face an opposing surface of each of, some of, or one of the plurality of securement members 440. In some embodiments, one of the inner surface or the outer surface of the occlusive element 420 (e.g., the membrane, the fabric, or the tissue element, etc.) may be in contact with a surface of the plurality of interconnected struts (e.g., an inner surface, an outer surface, etc.), and the other of the inner surface or the outer surface of the occlusive element 420 (e.g., the membrane, the fabric, or the tissue element, etc.) not in contact with the plurality of interconnected struts may lie flush against and/or be in contact with an opposing surface of each of, some of, or one of the plurality of securement members 440. In some embodiments, one of the inner surface or the outer surface of the occlusive element 420 (e.g., the membrane, the fabric, or the tissue element, etc.) may be in contact with a surface of the plurality of interconnected struts (e.g., an inner surface, an outer surface, etc.), and the other of the inner surface or the outer surface of the occlusive element 420 (e.g., the membrane, the fabric, or the tissue element, etc.) not in contact with the plurality of interconnected struts may face an opposing surface of each of, some of, or one of the plurality of securement members 440.

In some embodiments, the tip portion of the plurality of securement members 440 may be capable of piercing the occlusive element 420 (e.g., the membrane, the fabric, or the tissue element, etc.). In some embodiments, the occlusive element 420 (e.g., the membrane, the fabric, or the tissue element, etc.) may optionally include one or more holes or apertures configured to receive the tip portion and/or the body portion of each of, some of, or one of the plurality of securement members 440. Each of, some of, or one of the plurality of securement members 440 may extend through the occlusive element 420 (e.g., the membrane, the fabric, or the tissue element, etc.) at least once (e.g., from the inner surface to the outer surface, from the outer surface to the inner surface). In some embodiments, each of, some of, or one of the plurality of securement members 440 may extend through the occlusive element 420 (e.g., the membrane, the fabric, or the tissue element, etc.) two times, three times, four times, or more (e.g., from the inner surface to the outer surface, from the outer surface to the inner surface).

In some embodiments, the tip portion of each of, some of, or one of the plurality of securement members 440 may extend radially inward from the base portion. In some embodiments, the body portion of each of, some of, or one of the plurality of securement members 440 may extend radially inward from the base portion. In some embodiments, the tip portion of each of, some of, or one of the plurality of securement members 140 may extend radially outward from the base portion. In some embodiments, the body portion of each of, some of, or one of the plurality of securement members 140 may extend radially outward from the base portion.

In some embodiments, the tip portion of each of, some of, or one of the plurality of securement members 440 may alternatingly extend radially inward and radially outward from the base portion. In some embodiments, the body portion of each of, some of, or one of the plurality of securement members 440 may alternatingly extend radially inward and radially outward from the base portion. For example, a first securement member 440 may extend radially inward from the base portion, and a second adjacent securement member 440 may extend radially outward from the base portion, and so on circumferentially around and/or about the central longitudinal axis of the medical implant 400 and/or the expandable framework 410.

The body portion of each of the plurality of securement members 440 may be attached to the expandable framework 410 at the base portion of its respective securement member 440. In one example, the tip portion of each of the plurality of securement members 440 may be formed with a generally straight or spear shape such that a free end of the securement member 440 generally extends radially inward from the base portion and/or toward the central longitudinal axis. In some embodiments, each of, some of, or one of the plurality of securement members 440 may include at least one barb extending and/or projecting laterally and/or circumferentially from its respective securement member 440. In some embodiments, the at least one barb of the plurality of securement members 440 extending and/or projecting laterally and/or circumferentially from each of, some of, or one of the plurality of securement members 440 projects from the body portion and/or the tip portion of its respective securement member 440. Each of the at least one barb may project from the body portion and/or the tip portion of the plurality of securement members 440 in a circumferential direction around the expandable framework 410 and/or the central longitudinal axis of the medical implant 400. In at least some embodiments, the circumferential direction may be transverse, lateral, and/or generally perpendicular to the body portion and/or the tip portion of the plurality of securement members 440. Similar to above, in some embodiments, the at least one barb of each of, some of, or one of the plurality of securement members 440 does not extend outward of the plurality of interconnected struts. As such, the plurality of securement members 440 and/or the at least one barb of the plurality of securement members 440 may be incapable of engaging with, extending into, and/or piercing native tissue(s) disposed outside of the expandable framework 410 and/or the plurality of interconnected struts.

Each of the at least one barb of the plurality of securement members 440 may include a forward surface facing towards the tip portion of its respective securement member 440, and a rear surface facing towards the base portion and/or the body portion of its respective securement member 440. The forward surface may be positioned at an obtuse angle relative to the body portion and/or the tip portion of its respective securement member 440. For example, the forward surface may face distally and/or away from the base portion and/or the body portion, as well as circumferentially relative to the body portion of its respective securement member 440 and/or the central longitudinal axis of the medical implant 400. In at least some embodiments, the rear surface may be positioned at an obtuse angle relative to the body portion of its respective securement member 440, and the forward surface and the rear surface may be angled to face in a common and/or the same circumferential direction. For example, the rear surface may face proximally and/or toward the base portion and/or the body portion, as well as circumferentially relative to the body portion of its respective securement member 440 and/or the central longitudinal axis of the medical implant 100. Alternatively, in some embodiments, the rear surface may be positioned at an acute angle or a right angle relative to the body portion of its respective securement member 440, and in embodiments with the acute angle, the forward surface and the rear surface may be angled to face in opposing circumferential directions. An intersection of the forward surface with the rear surface may form a barb tip. In at least some embodiments, the barb tip may be rounded. For example, the barb tip may be formed with a radius of about 0.025 inches (0.635 mm), 0.015 inches (0.381 mm), 0.010 inches (0.254 mm), 0.005 inches (0.127 mm), 0.002 inches (0.0508 mm), 0.001 inches (0.0254 mm), or another suitable dimension as desired. Additional and/or other configurations are also contemplated, at least some of which are described herein.

In some embodiments, the occlusive element 420 (e.g., the membrane, the fabric, or the tissue element, etc.) may extend radially past at least some of the plurality of securement members 440. In some embodiments, the occlusive element 420 (e.g., the membrane, the fabric, or the tissue element, etc.) may extend radially past each and/or all of the plurality of securement members 440.

In some embodiments, the at least one barb on each of, some of, or one of the plurality of securement members 440 may be disposed outward of the occlusive element 420 (e.g., the membrane, the fabric, or the tissue element, etc.) and/or the outer surface of the occlusive element 420 (e.g., the membrane, the fabric, or the tissue element, etc.) while the base portion of its respective securement member 440 is disposed inward of the occlusive element 420 (e.g., the membrane, the fabric, or the tissue element, etc.) and/or the inner surface of the occlusive element 420 (e.g., the membrane, the fabric, or the tissue element, etc.). The at least one barb may serve to retain the occlusive element 420 (e.g., the membrane, the fabric, or the tissue element, etc.) on the expandable framework 410 and/or the plurality of securement members 440, thereby preventing the occlusive element 420 (e.g., the membrane, the fabric, or the tissue element, etc.) from working loose and/or releasing from the expandable framework 410 as the expandable framework 410 is shifted between the collapsed configuration and the expanded configuration. In some embodiments, attachment of the occlusive element 420 (e.g., the membrane, the fabric, or the tissue element, etc.) to the expandable framework 410 may be substantially devoid of sutures and/or adhesives.

Figure 11:
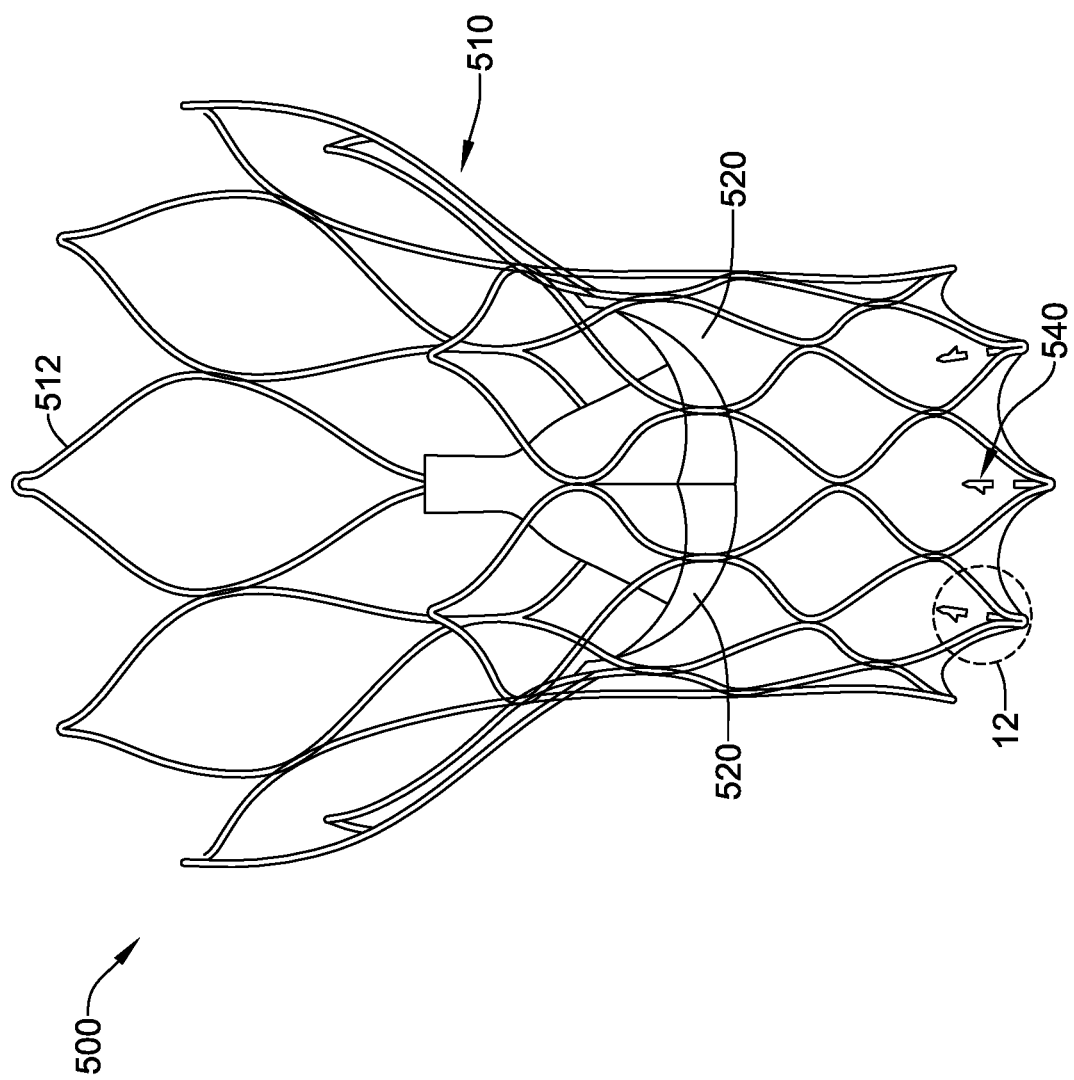
FIG. 11 schematically illustrates an example replacement heart valve implant.
Figure 12:
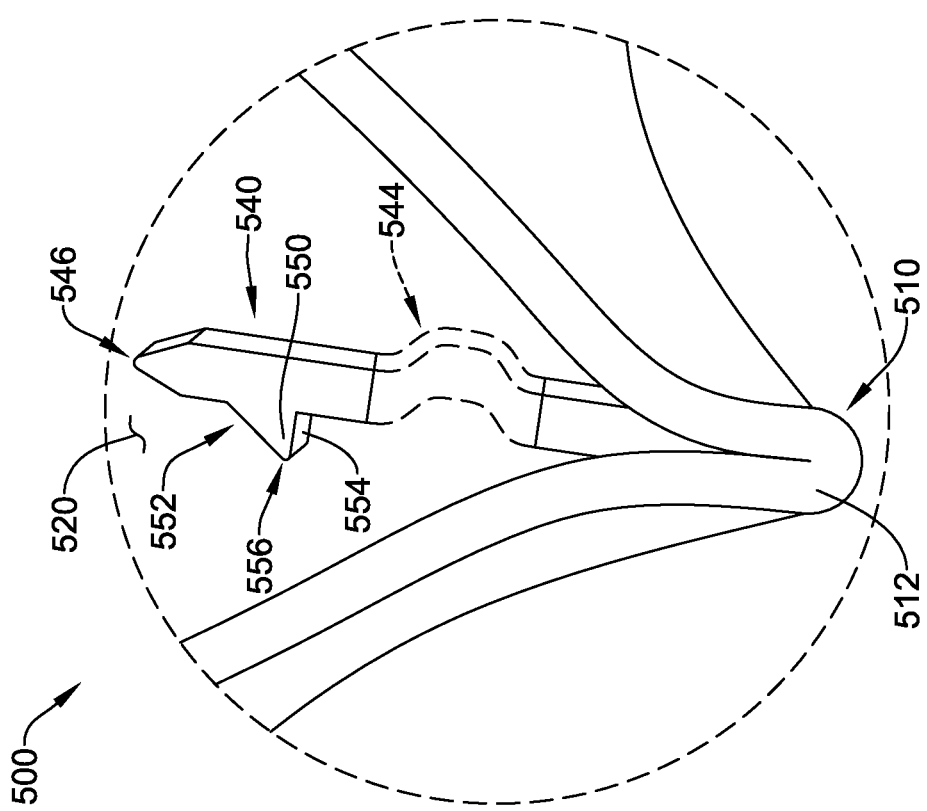
FIG. 12 is a detail view of a portion of the replacement heart valve implant of FIG. 11.

FIGS. 11 and 12 illustrate a replacement heart valve implant 500 that may benefit from use of the disclosed securement member(s). In some embodiments, the replacement heart valve implant 500 may include an expandable framework 510 configured to shift between a collapsed configuration and an expanded configuration, wherein the expandable framework 510 may comprise a plurality of interconnected struts 512 defining a plurality of plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements. In at least some embodiments, the replacement heart valve implant 500 may be configured for percutaneous delivery and implantation within a native heart valve and/or a native heart valve annulus of a patient. Other delivery means and/or methods are also contemplated.

The replacement heart valve implant 500 may include at least one valve leaflet 520 connected to the expandable framework 510 and/or the plurality of interconnected struts 512 and disposed within a lumen of the expandable framework 510. In some embodiments, the at least one valve leaflet 520 may include two valve leaflets, three valve leaflets, or another suitable number of valve leaflets.

In some embodiments, the replacement heart valve implant 500 and/or the expandable framework 510 may include a plurality of securement members 540 projecting from the plurality of interconnected struts 512. Each of the plurality of securement members 540 may include a base portion attached to the plurality of interconnected struts 512, a tip portion 546, and a body portion 544 extending from the base portion to the tip portion 546, as seen in FIG. 12 for example. In some embodiments, the tip portion 546 of each of, some of, or one of the plurality of securement members 540 may be radially aligned with the plurality of interconnected struts 512 (e.g., on a common circumference). In some embodiments, the body portion 544 and/or the tip portion 546 of the plurality of securement members 540 may be oriented substantially parallel to the plurality of interconnected struts 512. In some embodiments, the body portion 544 of each of, some of, or one of the plurality of securement members 540 may having an offset extending radially inward of the plurality of interconnected struts 512. In some embodiments, the at least one valve leaflet 520 (e.g., the occlusive element, etc.) may be disposed radially outward of the offset and/or the body portion 544 of each of, some of, or one of the plurality of securement members 540. In some embodiments, the offset may comprise a double offset, wherein the body portion 544 shifts radially inward relative to the plurality of interconnected struts 512 and then shifts again radially outward relative to the plurality of interconnected struts 512, such that the body portion 544 is radially offset from the plurality of interconnected struts 512 and the tip portion 546 is radially aligned with the plurality of interconnected struts 512 (e.g., on a common circumference). In some embodiments, the tip portion 546 of each of, some of, or one of the plurality of securement members 540 may be disposed radially outward of the at least one valve leaflet 520. In some embodiments, the tip portion 546 of each of, some of, or one of the plurality of securement members 540 may be radially offset from and substantially parallel to the body portion 544 of the plurality of securement members 540. In some embodiments, the tip portion 546 of each of, some of, or one of the plurality of securement members 540 does not extend radially outward of the plurality of interconnected struts 512. As such, the plurality of securement members 540 and/or the tip portion 546 of the plurality of securement members 540 may be incapable of engaging with, extending into, and/or piercing native tissue(s) disposed outside of (e.g., radially outward of, etc.) the expandable framework 510 and/or the plurality of interconnected struts 512.

In some embodiments, the at least one valve leaflet 520 may have an inner surface and an outer surface. In some embodiments, one of the inner surface or the outer surface of the at least one valve leaflet 520 may face towards a surface (e.g., an inner surface, an outer surface, etc.) of the plurality of interconnected struts 512, and the other of the inner surface or the outer surface of the at least one valve leaflet 520 not facing the plurality of interconnected struts 512 may face towards an opposing surface (e.g., an inner surface, an outer surface, etc.) of each of, some of, or one of the plurality of securement members 540 and/or the offset. For example, an outer surface of the at least one valve leaflet 520 may face towards an inner surface of the plurality of interconnected struts 512, and an inner surface of the at least one valve leaflet 520 may face towards an outer surface of each of, some of, or one of the plurality of securement members 540 and/or the body portion 544 of each of, some of, or one of the plurality of securement members 540.

In some embodiments, one of the inner surface or the outer surface of the at least one valve leaflet 520 may be in contact with a surface (e.g., the inner surface, the outer surface, etc.) of the plurality of interconnected struts 512, and the other of the inner surface or the outer surface of the at least one valve leaflet 520 not in contact with the plurality of interconnected struts 512 may lie flush against and/or be in contact with an opposing surface (e.g., the inner surface, the outer surface, etc.) of each of, some of, or one of the plurality of securement members 540 and/or the offset. For example, an outer surface of the at least one valve leaflet 520 may be in contact with an inner surface of the plurality of interconnected struts 512, and an inner surface of the at least one valve leaflet 520 may lie flush against and/or be in contact with an outer surface of each of, some of, or one of the plurality of securement members 540 and/or the body portion 544 of each of, some of, or one of the plurality of securement members 540 and/or the offset.

In some embodiments, one of the inner surface or the outer surface of the at least one valve leaflet 520 may be in contact with a surface (e.g., the inner surface, the outer surface, etc.) of the plurality of interconnected struts 512, and the other of the inner surface or the outer surface of the at least one valve leaflet 520 not in contact with the plurality of interconnected struts 512 may face an opposing surface (e.g., the inner surface, the outer surface, etc.) of each of, some of, or one of the plurality of securement members 540 and/or the offset. For example, an outer surface of the at least one valve leaflet 520 may be in contact with an inner surface of the plurality of interconnected struts 512, and an inner surface of the at least one valve leaflet 520 may face an opposing outer surface of each of, some of, or one of the plurality of securement members 540 and/or the body portion 544 of the plurality of securement members 540.

In some embodiments, the tip portion 546 of the plurality of securement members 540 may be capable of piercing the at least one valve leaflet 520. In some embodiments, the at least one valve leaflet 520 may optionally include one or more holes or apertures configured to receive the tip portion 546 and/or the body portion 544 of each of, some of, or one of the plurality of securement members 540. Each of, some of, or one of the plurality of securement members 540 may extend through the at least one valve leaflet 520 at least once (e.g., from the outer surface to the inner surface, etc.). In some embodiments, each of, some of, or one of the plurality of securement members 540 may extend through the at least one valve leaflet 520 two times, three times, four times, or more (e.g., from the outer surface to the inner surface and back again, etc.). In some embodiments, the at least one valve leaflet 520 may be disposed radially outward of the offset and/or the body portion 544 of each of, some of, or one of the plurality of securement members 540.

In some embodiments, the tip portion 546 of each of, some of, or one of the plurality of securement members 540 may extend axially toward the inflow end of the at least one valve leaflet 520 and/or the expandable framework 510. In some embodiments, the body portion 544 of each of, some of, or one of the plurality of securement members 540 may extend axially toward the inflow end of the at least one valve leaflet 520 and/or the expandable framework 510. In some embodiments, the tip portion 546 of each of, some of, or one of the plurality of securement members 540 may extend axially toward the outflow end of the at least one valve leaflet 520 and/or the expandable framework 510. In some embodiments, the body portion 544 of each of, some of, or one of the plurality of securement members 540 may extend axially toward the outflow end of the at least one valve leaflet 520 and/or the expandable framework 510.

In some embodiments, the tip portion 546 of each of, some of, or one of the plurality of securement members 540 may alternatingly extend axially toward the inflow end and the outflow end of the at least one valve leaflet 520 and/or the expandable framework 510. In some embodiments, the body portion 544 of each of, some of, or one of the plurality of securement members 540 may alternatingly extend axially toward the inflow end and the outflow end of the at least one valve leaflet 520 and/or the expandable framework 510. For example, a first securement member 540 may extend axially toward the inflow end of the at least one valve leaflet 520 and/or the expandable framework 510, and a second adjacent securement member 540 may extend axially toward the outflow end of the at least one valve leaflet 520 and/or the expandable framework 510, and so on circumferentially around and/or about the expandable framework 510.

The body portion 544 of each of the plurality of securement members 540 may be attached to the expandable framework 510 at the base portion of its respective securement member 540. In one example, the tip portion 546 of each of the plurality of securement members 540 may be formed with a generally straight or spear shape such that a free end of the securement member 540 generally extends axially and/or toward the outflow end the at least one valve leaflet 520 and/or the expandable framework 510. Other orientations are also contemplated as discussed herein.

In some embodiments, each of, some of, or one of the plurality of securement members 540 may include at least one barb 550 extending and/or projecting laterally and/or circumferentially from its respective securement member 540. In some embodiments, the at least one barb 550 of the plurality of securement members 540 extending and/or projecting laterally and/or circumferentially from each of, some of, or one of the plurality of securement members 540 projects from the body portion 544 and/or the tip portion 546 of its respective securement member 540. Each of the at least one barb 550 may project from the body portion 544 and/or the tip portion 546 of the plurality of securement members 540 in a circumferential direction around the expandable framework 510 and/or a central longitudinal axis of the replacement heart valve implant 500. In at least some embodiments, the circumferential direction may be transverse, lateral, and/or generally perpendicular to the body portion 544 and/or the tip portion 546 of the plurality of securement members 540.

Each of the at least one barb 550 of the plurality of securement members 540 may include a forward surface 552 facing towards the tip portion 546 of its respective securement member 540, and a rear surface 554 facing towards the base portion and/or the body portion 544 of its respective securement member 540. The forward surface 552 may be positioned at an obtuse angle relative to the body portion 544 and/or the tip portion 546 of its respective securement member 540. For example, the forward surface 552 may face distally and/or away from the base portion and/or the body portion 544, as well as circumferentially relative to the body portion 544 of its respective securement member 540 and/or the central longitudinal axis of the replacement heart valve implant 500. In at least some embodiments, the rear surface 554 may be positioned at an obtuse angle relative to the body portion 544 of its respective securement member 540, and the forward surface 552 and the rear surface 554 may be angled to face in a common and/or the same circumferential direction. For example, the rear surface 554 may face proximally and/or toward the base portion and/or the body portion 544, as well as circumferentially relative to the body portion 544 of its respective securement member 540 and/or the central longitudinal axis of the replacement heart valve implant 500. Alternatively, in some embodiments, the rear surface 554 may be positioned at an acute angle or a right angle relative to the body portion 544 of its respective securement member 540, and in embodiments with the acute angle, the forward surface 552 and the rear surface 554 may be angled to face in opposing circumferential directions. An intersection of the forward surface 552 with the rear surface 554 may form a barb tip 556. In at least some embodiments, the barb tip 556 may be rounded. For example, the barb tip 556 may be formed with a radius of about 0.025 inches (0.635 mm), 0.015 inches (0.381 mm), 0.010 inches (0.254 mm), 0.005 inches (0.127 mm), 0.002 inches (0.0508 mm), 0.001 inches (0.0254 mm), or another suitable dimension as desired. Additional and/or other configurations are also contemplated, at least some of which are described herein.

In some embodiments, the at least one valve leaflet 520 may extend axially past at least some of the plurality of securement members 540. In some embodiments, the at least one valve leaflet 520 may extend axially past each and/or all of the plurality of securement members 540.

In some embodiments, the at least one barb 550 on each of, some of, or one of the plurality of securement members 540 may be disposed radially outward of the at least one valve leaflet 520 and/or the outer surface of the at least one valve leaflet 520 while the base portion of its respective securement member 540 is disposed radially inward of the at least one valve leaflet 520 and/or the inner surface of the at least one valve leaflet 520. The at least one barb 550 may serve to retain the at least one valve leaflet 520 on the expandable framework 510 and/or the plurality of securement members 540, thereby preventing the at least one valve leaflet 520 from working loose and/or releasing from the expandable framework 510 as the expandable framework 510 is shifted between the collapsed configuration and the expanded configuration. In some embodiments, attachment of the at least one valve leaflet 520 to the expandable framework 510 may be substantially devoid of sutures and/or adhesives.

FIGS. 13-19 illustrate several different configurations for the at least one barb 150/250/350/550 described in conjunction with the plurality of securement members 140/240/340/440/540 discussed herein. While the following examples are described using reference numerals 6XX, it is to be understood that any and/or all of the examples may be used interchangeably with any and/or all of the above-described at least one barb 150/250/350/550 and/or the plurality of securement members 140/240/340/440/540. Other configurations, orientations, and/or modifications are also contemplated.

As described herein, the at least one barb 650 projects circumferentially from each of, some of, or one of the plurality of securement members 640 and in some embodiments may project from the body portion 644 of its respective securement member 640. The at least one barb 650 may include the forward surface 652 facing towards the tip portion 646 of its respective securement member 640, and the rear surface 654 facing towards the base portion 642 and/or the body portion 644 of its respective securement member 640. The intersection of the forward surface 652 with the rear surface 654 may form a barb tip 656, and in at least some embodiments, the barb tip 656 may be rounded. In some embodiments, the at least one barb 650 may be configured such that the occlusive element 120/220/320/420/520 (e.g., the membrane, the fabric, the tissue element, the at least one heart valve leaflet, etc.) may be manually removed from the plurality of securement members 640 by a technician or operator by manipulating that the occlusive element 120/220/320/420/520 (e.g., the membrane, the fabric, the tissue element, the at least one heart valve leaflet, etc.) over and/or around the at least one barb 650, but that the occlusive element 120/220/320/420/520 (e.g., the membrane, the fabric, the tissue element, the at least one heart valve leaflet, etc.) is incapable of coming off (e.g., falling off, etc.) of the plurality of securement members 640 on its own.

In some embodiments, the forward surface 652 may be positioned and/or arranged at an obtuse angle to an axis of the body portion 644 of its respective securement member 640. In some embodiments, the forward surface 652 may be positioned and/or arranged at an angle of about 130 to about 170 degrees, about 140 to about 160 degrees, about 150 degrees, etc. relative to the axis of the body portion 644 of its respective securement member 640.

Figure 13:
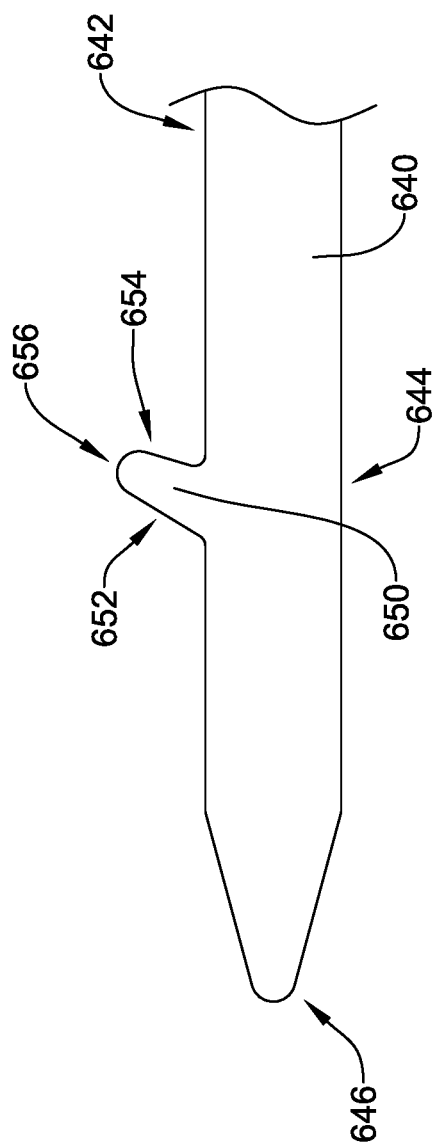
FIGS. 13-19 illustrate alternative configurations of a securement member.

In some embodiments, the rear surface 654 may be positioned and/or arranged at an acute angle to the axis of the body portion 644 of its respective securement member 640, as seen in FIG. 13 for example. In some embodiments, the rear surface 654 may be positioned and/or arranged at an angle of about 30 to about 85 degrees, about 45 to about 60 degrees, etc. relative to the axis of the body portion 644 of its respective securement member 640.

Figure 14:
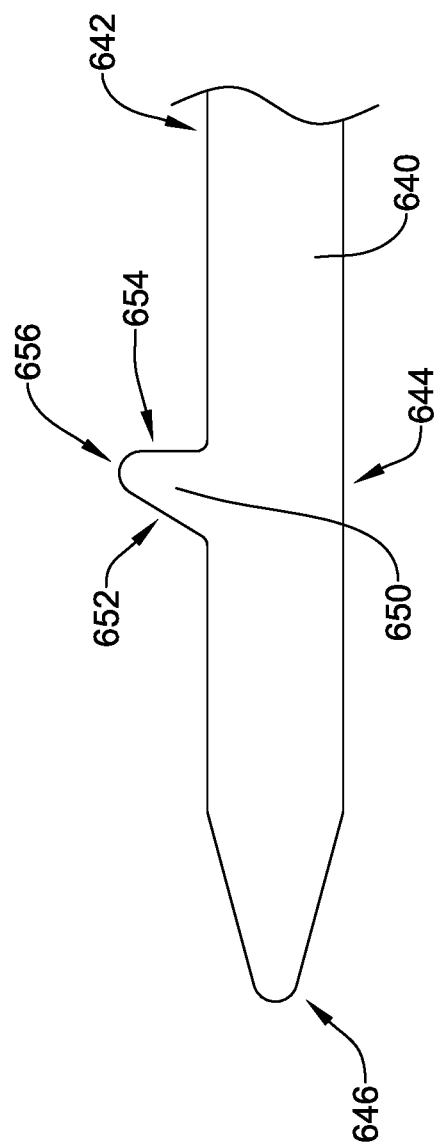

In some embodiments, the rear surface 654 may be positioned and/or arranged at a generally right angle to the axis of the body portion 644 of its respective securement member 640, as seen in FIG. 14 for example. In some embodiments, the rear surface 654 may be positioned and/or arranged at an angle of about 85 to about 95 degrees, etc. relative to the axis of the body portion 644 of its respective securement member 640.

Figure 15:
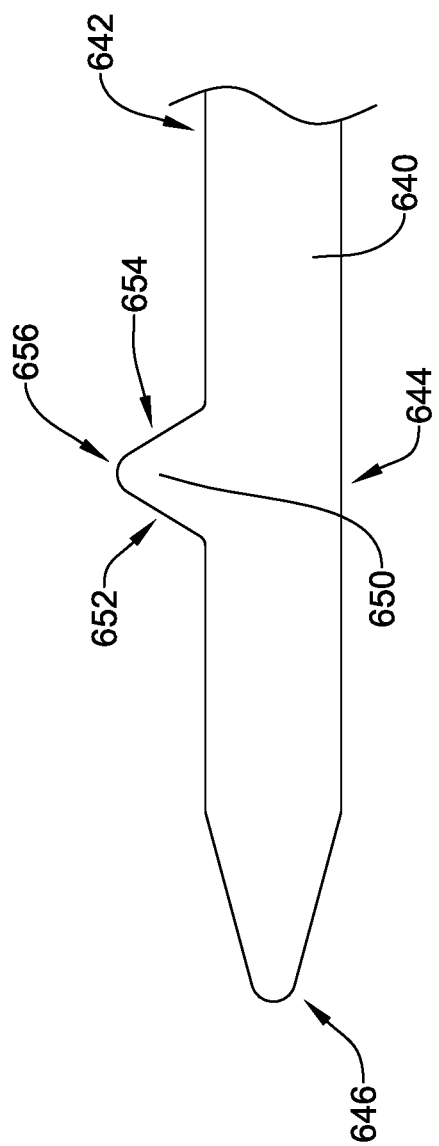

In some embodiments, the rear surface 654 may be positioned and/or arranged at an obtuse angle to the axis of the body portion 644 of its respective securement member 640, as seen in FIG. 15 for example. In some embodiments, the rear surface 654 may be positioned and/or arranged at an angle of about 95 to about 130 degrees, about 100 to about 120 degrees, etc. relative to the axis of the body portion 644 of its respective securement member 640.

Figure 16:
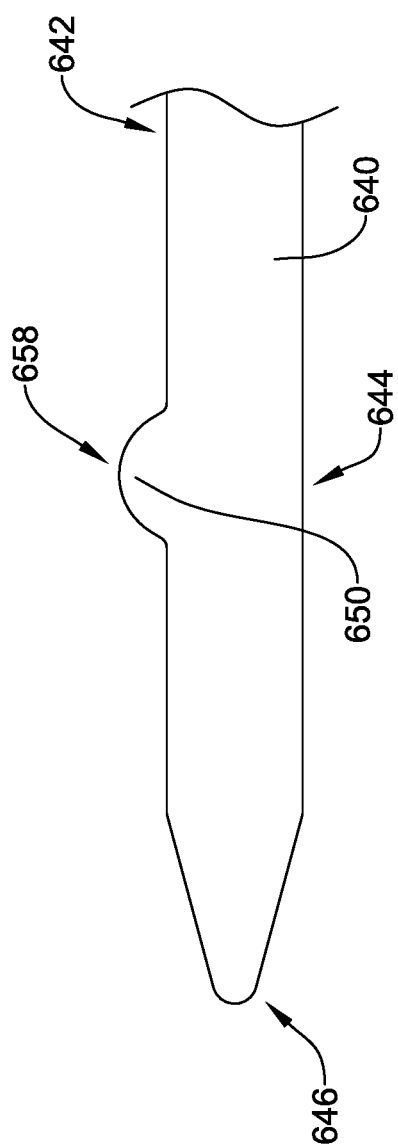

In one alternative embodiment, the at least one barb 650 may include and/or be formed as a semi-elliptical nub 658, as seen in FIG. 16 for example. In some embodiments, the at least one barb 650 may include two barbs 650 projecting circumferentially from each of, some of, or one of the plurality of securement members 640. In one example, each barb may comprise the semi-elliptical nub 658, wherein each semi-elliptical nub 658 on a particular securement member 640 extends in a common circumferential direction from the particular securement member 640. In another alternative example, each of the two barbs 650 may be semi-elliptical nubs extending in opposing circumferential directions from their respective securement member 640.

Figure 17:
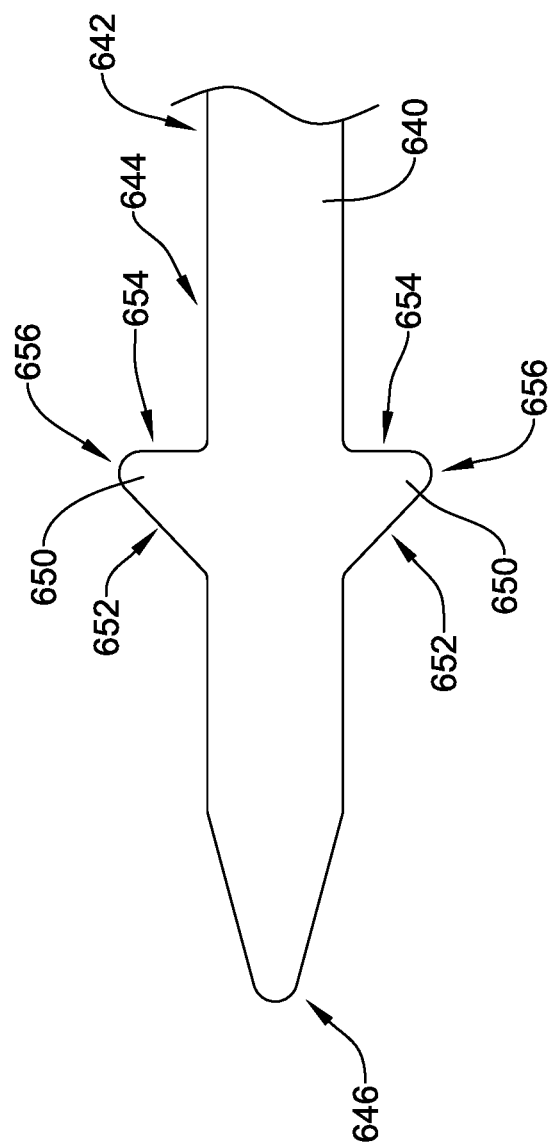
Figure 18:
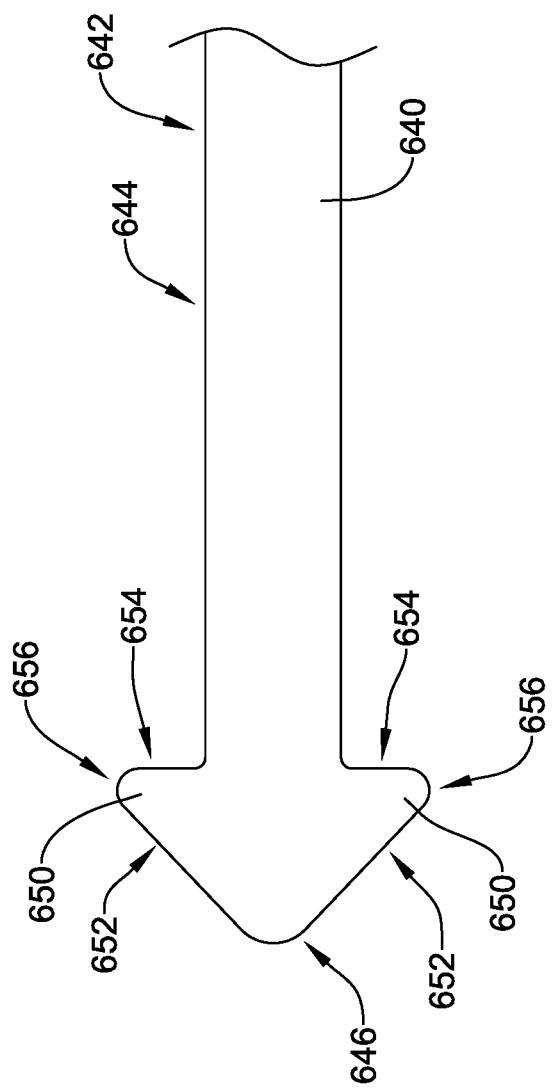

In some embodiments, the at least one barb 650 may include two barbs 650 projecting circumferentially from each of, some of, or one of the plurality of securement members 640. In some embodiments, the two barbs 650 may extend in opposing circumferential directions from their respective securement member 640 as substantially mirror images of each other in an "arrowhead" configuration, wherein each barb may include the forward surface 652 facing towards the tip portion 646 of its respective securement member 640, and the rear surface 654 facing towards the base portion 642 and/or the body portion 644 of its respective securement member 640, as seen in FIG. 17, wherein the two barbs 650 extend from the body portion 644, and FIG. 18, wherein the two barbs 650 extend from and/or be positioned adjacent to the tip portion 646, for example.

In another alternative example, each of, some of, or one of the plurality of securement members 640 may be formed with an undulating S-curve or zigzagging shape forming a plurality of projections extending transverse to the axis of the securement member 640. The plurality of projections could be formed in a radial direction relative to the central longitudinal axis of the medical implant, a circumferential direction relative to the central longitudinal axis of the medical implant, both radial and circumferential directions relative to the central longitudinal axis of the medical implant, or in other configurations. Other configurations and/or arrangements are also contemplated.

Figure 19:
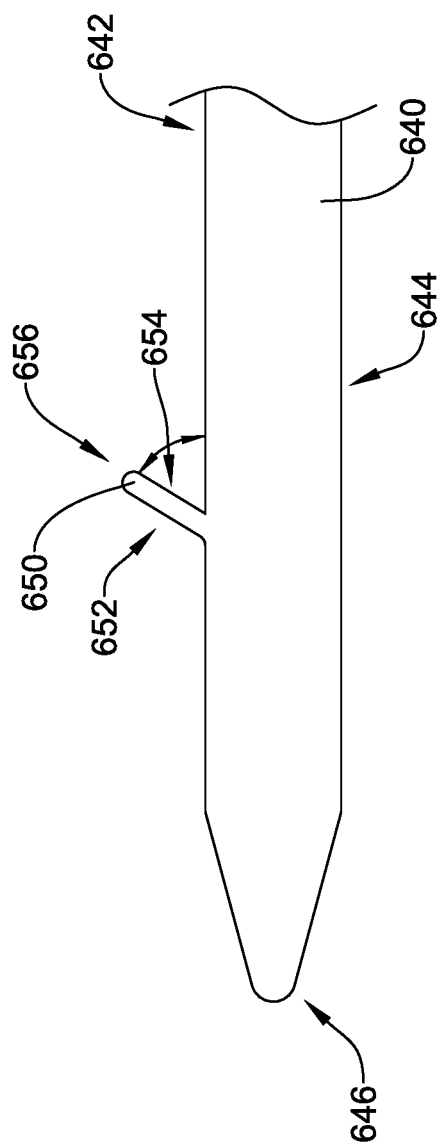

In another example, the rear surface 654 may be positioned and/or arranged at an acute angle to the axis of the body portion 644 of its respective securement member 640. In some embodiments, the rear surface 654 may be positioned and/or arranged at an angle of about 30 to about 85 degrees, about 45 to about 60 degrees, etc. relative to the axis of the body portion 644 of its respective securement member 640. Additionally, the at least one barb 650 may be configured to bend, flex, and/or pivot relative to its respective securement member 640, as seen in FIG. 19 for example. In some embodiments, the at least one barb 650 may include two barbs 650 projecting circumferentially from each of, some of, or one of the plurality of securement members 640. In some embodiments, the two barbs 650 may extend in opposing circumferential directions from their respective securement member 640 as substantially mirror images of each other. The at least one barb 650 being configured to bend, flex, and/or pivot may permit the at least one barb 650 to deflect inward toward the respective securement member 640 and/or the body portion 644 of the securement member 640 to reduce the size of the securement member 640 during assembly for example. Other configurations and/or benefits are also contemplated.

The materials that can be used for the various components of the medical device system, the core wire, the catheter, the medical implant, the expandable framework, the occlusive element, the membrane, the fabric, the tissue element, the plurality of securement members, the at least one barb, etc. (and/or other systems or components disclosed herein) and the various elements thereof disclosed herein may include those commonly associated with medical devices. For simplicity purposes, the following discussion makes reference to the medical device system, the core wire, the catheter, the medical implant, the expandable framework, the occlusive element, the membrane, the fabric, the tissue element, the plurality of securement members, the at least one barb, etc. However, this is not intended to limit the devices and methods described herein, as the discussion may be applied to other elements, members, components, or devices disclosed herein, such as, but not limited to, the plurality of interconnected struts, the base portion, the body portion, the tip portion, the barb, the forward surface, the rear surface, the barb tip, etc. and/or elements or components thereof.

In some embodiments, the medical device system, the core wire, the catheter, the medical implant, the expandable framework, the occlusive element, the membrane, the fabric, the tissue element, the plurality of securement members, the at least one barb, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system, the core wire, the catheter, the medical implant, the expandable framework, the occlusive element, the membrane, the fabric, the tissue element, the plurality of securement members, the at least one barb, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system, the core wire, the catheter, the medical implant, the expandable framework, the occlusive element, the membrane, the fabric, the tissue element, the plurality of securement members, the at least one barb, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system, the core wire, the catheter, the medical implant, the expandable framework, the occlusive element, the membrane, the fabric, the tissue element, the plurality of securement members, the at least one barb, etc. to achieve the same result.

In some embodiments, a degree of Magnetic Resonance Imaging (MRI) compatibility is imparted into the medical device system, the core wire, the catheter, the medical implant, the expandable framework, the occlusive element, the membrane, the fabric, the tissue element, the plurality of securement members, the at least one barb, etc. For example, the medical device system, the core wire, the catheter, the medical implant, the expandable framework, the occlusive element, the membrane, the fabric, the tissue element, the plurality of securement members, the at least one barb, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system, the core wire, the catheter, the medical implant, the expandable framework, the occlusive element, the membrane, the fabric, the tissue element, the plurality of securement members, the at least one barb, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system, the core wire, the catheter, the medical implant, the expandable framework, the occlusive element, the membrane, the fabric, the tissue element, the plurality of securement members, the at least one barb, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the medical implant, the expandable framework, the occlusive element, the membrane, the fabric, the tissue element, etc. disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system, the medical implant, the expandable framework, the occlusive element, the membrane, the fabric, the tissue element, etc. may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system, the core wire, the catheter, the medical implant, the expandable framework, the occlusive element, the membrane, the fabric, the tissue element, the plurality of securement members, the at least one barb, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

While the discussion above is generally directed toward an occlusive implant for use in the left atrial appendage of the heart and/or a replacement heart valve implant, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), other replacement valve implants (e.g., replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical implant, comprising:
an expandable framework configured to shift between a collapsed configuration and an expanded configuration, the expandable framework comprising a plurality of interconnected struts defining a plurality of cells; and
an occlusive element connected to the expandable framework and having an inner surface and an outer surface;
wherein the expandable framework includes a plurality of securement members projecting from the plurality of interconnected struts;
wherein each of the plurality of securement members includes a base portion attached to at least one of the plurality of interconnected struts, a tip portion, and a body portion extending between the base portion and the tip portion, wherein some of the plurality of securement members extend through the occlusive member such that the base portion and the tip portion extend along the inner surface of the occlusive element, and part of the body portion extends along the outer surface of the occlusive element;
wherein the body portion is offset radially outward from the tip portion.

2. The medical implant of claim 1, wherein the tip portion is circumferentially aligned with the plurality of interconnected struts.

3. The medical implant of claim 1, wherein the tip portion extends axially toward an inflow end of the occlusive element.

4. The medical implant of claim 1, wherein the body portion extends axially toward an inflow end of the occlusive element.

5. The medical implant of claim 1, wherein at least some of the plurality of securement members each have a barb projecting circumferentially therefrom.

6. The medical implant of claim 5, wherein the barb projecting circumferentially from at least some of the plurality of securement members projects from the body portion of its respective securement member.

7. The medical implant of claim 5, wherein each barb includes a forward surface facing towards the tip portion of its respective securement member, and a rear surface facing towards the base of its respective securement member.

8. The medical implant of claim 7, wherein the rear surface is positioned at an obtuse angle to the body portion.

9. The medical implant of claim 7, wherein the rear surface is positioned at an acute angle to the body portion.

10. The medical implant of claim 7, wherein the forward surface is positioned at an obtuse angle to the body portion.

11. The medical implant of claim 5, wherein the barb on at least some of the plurality of securement members is configured to engage native tissue when the medical implant is expanded at a target site.

12. The medical implant of claim 1, wherein the expandable framework and the plurality of securement members are formed from a unitary tubular member.

13. The medical implant of claim 1, wherein the inner surface of the occlusive element is in contact with an outer surface of the plurality of interconnected struts, and the outer surface of the occlusive element lies against an inner surface of the body portion of the plurality of securement members.

14. A medical implant, comprising:
an expandable framework configured to shift between a collapsed configuration and an expanded configuration, the expandable framework comprising a plurality of interconnected struts defining a plurality of cells; and
an occlusive element connected to the expandable framework and having an inner surface and an outer surface;
wherein the expandable framework includes a plurality of securement members projecting from the plurality of interconnected struts;
wherein one of the inner surface or the outer surface of the occlusive element is in contact with the plurality of interconnected struts, and the other of the inner surface or the outer surface not in contact with the plurality of interconnected struts lies against an opposing surface of each of the plurality of securement members;
wherein each of the plurality of securement members includes a body portion and a tip portion, wherein when in the expanded configuration the tip portion extends axially from the body portion and the tip portion is not disposed radially outward of the plurality of interconnected struts;
wherein in the expanded configuration the body portion is disposed radially outward of the plurality of interconnected struts;
wherein at least some of the plurality of securement members have a barb projecting laterally therefrom, the barb positioned adjacent the tip portion.

15. The medical implant of claim 14, wherein the occlusive element is disposed radially inward of the body portion.

16. The medical implant of claim 15, wherein the inner surface of the occlusive element is in contact with the plurality of interconnected struts, and the outer surface of the occlusive element faces an inner surface of the body portion.

17. The medical implant of claim 14, wherein the barb on at least some of the plurality of securement members is configured to engage native tissue when the medical implant is expanded at a target site.

18. The medical implant of claim 14, wherein the tip portion is configured to pierce the occlusive element.

19. A medical implant, comprising:
an expandable framework configured to shift between a collapsed configuration and an expanded configuration, the expandable framework comprising a plurality of interconnected struts defining a plurality of cells; and
an occlusive element connected to the expandable framework and having an inner surface and an outer surface;
wherein the expandable framework includes a plurality of securement members projecting from the plurality of interconnected struts;
wherein each of the plurality of securement members includes a body portion and a tip portion, wherein when in the expanded configuration the tip portion extends axially from the body portion and is configured to pierce the occlusive element;
wherein at least some of the plurality of securement members have a barb projecting therefrom, the barb positioned adjacent the tip portion, wherein at least some of the barbs are configured to engage native tissue when the medical implant is expanded at a target site;
wherein in the expanded configuration the body portion is disposed radially outward of the tip portion.

* * * * *